United States Patent
Zhou et al.

(10) Patent No.: US 11,864,939 B2
(45) Date of Patent: *Jan. 9, 2024

(54) APPARATUS AND METHOD THAT USES DEEP LEARNING TO CORRECT COMPUTED TOMOGRAPHY (CT) WITH SINOGRAM COMPLETION OF PROJECTION DATA

(71) Applicant: CANON MEDICAL SYSTEMS CORPORATION, Otawara (JP)

(72) Inventors: Jian Zhou, Buffalo Grove, IL (US); Ruoqiao Zhang, Arlington Heights, IL (US); Zhou Yu, Wilmette, IL (US); Yan Liu, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 238 days.

This patent is subject to a terminal disclaimer.

(21) Appl. No.: 17/339,093

(22) Filed: Jun. 4, 2021

(65) Prior Publication Data

US 2021/0290193 A1    Sep. 23, 2021

Related U.S. Application Data

(63) Continuation of application No. 16/227,251, filed on Dec. 20, 2018, now Pat. No. 11,039,806.

(51) Int. Cl.
*A61B 6/00* (2006.01)
*G06T 11/00* (2006.01)
(Continued)

(52) U.S. Cl.
CPC .......... *A61B 6/5258* (2013.01); *A61B 6/4014* (2013.01); *G06N 3/045* (2023.01);
(Continued)

(58) Field of Classification Search
CPC ... A61B 6/5258; A61B 6/4014; A61B 6/4241; A61B 6/032; A61B 6/482; A61B 6/5205;
(Continued)

(56) References Cited

U.S. PATENT DOCUMENTS 11,039,806 B2 * 6/2021 Zhou .................. G06T 5/10
2011/0052022 A1   3/2011 Xu et al.
(Continued)

FOREIGN PATENT DOCUMENTS

JP        2004-188187 A    7/2004
WO    WO 2012/104740 A1   8/2012
(Continued)

OTHER PUBLICATIONS

Xu et al. "Image Decomposition Algorithm for Dual-Energy Computed Tomography via Fully Convolutional Network." Hindawi, Computational and Mathematical Methods in Medicine, vol. 2018, Article ID 2527516, https://doi.org/10.1155/2018/2527516, Sep. 5, 2018, pp. 1-9 (Year: 2018).*

(Continued)

*Primary Examiner* — Jon Chang
(74) *Attorney, Agent, or Firm* — Oblon, McClelland, Maier & Neustadt, L.L.P.

(57) ABSTRACT

A deep learning (DL) network corrects/performs sinogram completion in computed tomography (CT) images based on complementary high- and low-kV projection data generated from a sparse (or fast) kilo-voltage (kV)-switching CT scan. The DL network is trained using inputs and targets, which respectively generated with and without kV switching. Another DL network can be trained to correct sinogram-completion errors in the projection data after a basis/material decomposition. A third DL network can be trained to correct sinogram-completion errors in reconstructed images based on the kV-switching projection data. Performance of the DL (Continued)

network can be improved by dividing a 3D convolutional neural network (CNN) into two steps performed by respective 2D CNNs. Further, the projection data and DLL can be divided into high- and low-frequency components to improve performance.

20 Claims, 22 Drawing Sheets

(51) Int. Cl.
<table>
<tr><td>G06T 5/50</td><td>(2006.01)</td></tr>
<tr><td>G06T 5/20</td><td>(2006.01)</td></tr>
<tr><td>G06T 5/10</td><td>(2006.01)</td></tr>
<tr><td>G06N 3/084</td><td>(2023.01)</td></tr>
<tr><td>G06N 3/045</td><td>(2023.01)</td></tr>
</table>

(52) U.S. Cl.
CPC ............... *G06N 3/084* (2013.01); *G06T 5/10* (2013.01); *G06T 5/20* (2013.01); *G06T 5/50* (2013.01); *G06T 11/005* (2013.01); *G06T 11/006* (2013.01); *G06T 11/008* (2013.01); *A61B 6/482* (2013.01); *A61B 6/5205* (2013.01); *G06T 2207/10081* (2013.01); *G06T 2207/20064* (2013.01); *G06T 2207/20081* (2013.01); *G06T 2207/20084* (2013.01); *G06T 2211/408* (2013.01)

(58) Field of Classification Search
CPC ........ A61B 6/035; G06N 3/045; G06N 3/084; G06T 5/10; G06T 5/20; G06T 5/50; G06T 11/005; G06T 11/006; G06T 11/008; G06T 2207/10081; G06T 2207/20064; G06T 2207/20081; G06T 2207/20084; G06T 2211/408; G06T 2211/441; G06T 2207/20224
See application file for complete search history.

(56) References Cited

U.S. PATENT DOCUMENTS

<table>
<tr><td>2013/0308745 A1</td><td>11/2013</td><td>Goshen</td></tr>
<tr><td>2017/0365075 A1</td><td>12/2017</td><td>Meganck et al.</td></tr>
<tr><td>2019/0251713 A1</td><td>8/2019</td><td>Chen</td></tr>
<tr><td>2019/0325621 A1</td><td>10/2019</td><td>Wang et al.</td></tr>
<tr><td>2019/0328348 A1</td><td>10/2019</td><td>De Man</td></tr>
<tr><td>2019/0371018 A1</td><td>12/2019</td><td>Ye</td></tr>
<tr><td>2020/0015772 A1</td><td>1/2020</td><td>Roeske</td></tr>
<tr><td>2020/0273214 A1*</td><td>8/2020</td><td>Xu ............................ G06N 3/08</td></tr>
</table>

FOREIGN PATENT DOCUMENTS

<table>
<tr><td>WO</td><td>WO 2016-175755 A1</td><td>11/2016</td></tr>
<tr><td>WO</td><td>WO 2017/214048 A1</td><td>12/2017</td></tr>
<tr><td>WO</td><td>WO 2017/223560 A1</td><td>12/2017</td></tr>
</table>

OTHER PUBLICATIONS

Zhang et al. "Model-Based Iterative Reconstruction for Dual-Energy X-Ray CT Using a Joint Quadratic Likelihood Model." IEEE Transactions on Medical Imaging, vol. 33, No. 1, Jan. 2014, pp. 117-134 (Year: 2014).*
Liu et al. "A Low-Cost Dual Energy CT System with Sparse Data." Tsinghua Science and Technology, vol. 19, iss.2, Apr. 15, 2014, pp. 184-194 (Year: 2014).*
Guy et al. "DETECT—Dual Energy Transmission Estimation CT—for Improved Attenuation Correction in SPECT and PET." IEEE Nuclear Science Symposium Conference Record, Nov. 9, 1997, pp. 1595-1599 (Year: 1997).*
K. Kim, et al, "Sparse-View Spectral CT Reconstruction Using Spectral Patch-Based Low-Rank Penalty". IEEE Transactions on Medical Imaging, vol. 34, No. 3, Mar. 2015.
W. Huh, et al, "Iterative image reconstruction for dual-energy X-ray CT using regularized material sinogram estimates" IEEE, ISBI 2011.
R. Barber, et al, "An algorithm for constrained one-step inversion of spectral CT data", IPEM: Physics in Medicine & Biology, vol. 61, PMB 2016.
H. Lee, et al, "View-interpolation of sparsely sampled sinogram using convolutional neural network", Event: SPIE Medical Imaging, Orlando, Florida, 2017.
Extended European Search Report dated Apr. 29, 2020 in European Patent Application No. 19216170.1, 9 pages.
Hoyeon, L., et al., "View-interpolation of sparsely sampled sinogram using convolutional neural network", Progress in Biomedical Optics and Imaging, SPIE—International Society for Optical Engineering, vol. 10133, Feb. 24, 2017, XP060086982, pp. 1013328-1-1013328-8.
Ghani et al, "Deep Learning-Based Sinogram Completion for Low-Dose CT," IEEE 13th Image, Video and Multidimensional Signal Processing Workshop, Jun. 10, 2018, 5 pages (Year: 2018).
Japanese Office Action dated Jan. 31, 2023 in Japanese Patent Application No. 2019-053607, 3 pages.

* cited by examiner

APPARATUS AND METHOD THAT USES DEEP LEARNING TO CORRECT COMPUTED TOMOGRAPHY (CT) WITH SINOGRAM COMPLETION OF PROJECTION DATA

CROSS-REFERENCE TO RELATED APPLICATIONS

This application is a continuation of and claims the benefit of U.S. Application Ser. No. 16/227,251, filed on Dec. 20, 2018; the entire of contents of which are incorporated herein by reference.

FIELD

This disclosure relates to using deep learning (DL) networks to reconstruct a computed tomography (CT) image from dual-energy (DE) projection data generated via kilo-voltage (kV)-switching, and, more particularly, to using deep learning (DL) to reduce errors and aid in sinogram completion to fill in projection values at missing projection angles (views).

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Computed tomography (CT) systems and methods are widely used, particularly for medical imaging and diagnosis. CT systems generally create images of one or more sectional slices through a subject's body. A radiation source, such as an X-ray tube, irradiates the body from one side. The attenuation of the radiation that has passed through the body is measured by processing electrical signals received from the detector, which are then used to reconstruct an image of the body by performing an inverse Radon transformation (or an equivalent thereof).

Both energy-integrating detectors and photon-counting detectors can be used in respective CT configurations to generate dual-energy CT (DE) (sometimes referred to as (spectral CT). DECT can advantageously be used to perform material decompositions, whereby bone can be distinguished from soft tissues in the body to provide more clinical information. Various configurations can be used for spectral imaging in CT. In general, the spectral CT configurations breakdown into two types. (i) at the X-ray source, generating different energy spectra (e.g., fast kilo-voltage (kV)-switching, and dual source configurations), and (ii) at the detector, distinguishing between detected X-ray based on their respective energies (e.g., dual layer detectors). Herein, the phrases "kilo-voltage peak" and "kilo-voltage" are used interchangeably in the context of switching the voltage applied to a X-ray source (e.g., X-ray tube) as a mechanism for controlling a spectrum of the X-rays radiating from the X-ray source.

More particularly, there are three DECT configurations of clinical significance: dual-layer detector systems, dual source systems, and fast kV-switching systems. For example, a dual-layer detector is one type of energy resolving detector. Dual-layer detectors use various X-ray energy filters arranged in front of respective energy integrating detectors, such that the filters perform the function of separating the detected X-rays into different energy bands.

Another DECT configuration is the dual X-ray source system. In the dual X-ray source system, two X-ray sources are arranged opposite respective detectors, each source-detector pair forming its own CT system, which operates simultaneously with the other CT system but with a different X-ray spectrum. For example, the two CT systems can be fixed to the same rotating annular ring with the gantry, but arranged at right angles with respect to each other. Accordingly, with this arrangement, two CT scans can be performed simultaneously with two different X-ray spectra.

In a third DECT configuration, a single integrating source can be used with an X-ray source (e.g., X-ray tube) that uses fast kV-switching to rapidly alternate between a high-energy X-ray spectrum and low-energy X-ray spectrum as the view angle of the CT scanner rotates around the patient.

Each of these three DECT architectures (i.e., dual-layer, dual-source, and kV-switching) has its own shortcomings. In dual-layer detector systems, the combination of scintillators and photo-multiplier tubes suffer from low-energy noise and from being poorly optimized to achieve out-of-band energy suppression. Further, energy separation is degraded by the significant overlap between the two readout spectra. The dual-source systems suffer from the added cost of a second system, and suffer from cross-scatter effects. The fast kV-switching systems also incur substantial additional costs due to requirements for an ultra-high frequency generator and parallel data acquisition systems (DASs) used to acquire in parallel the high-energy and low-energy projection data.

Accordingly, a better spectral CT approach is desired that overcomes the above-identified deficiencies.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
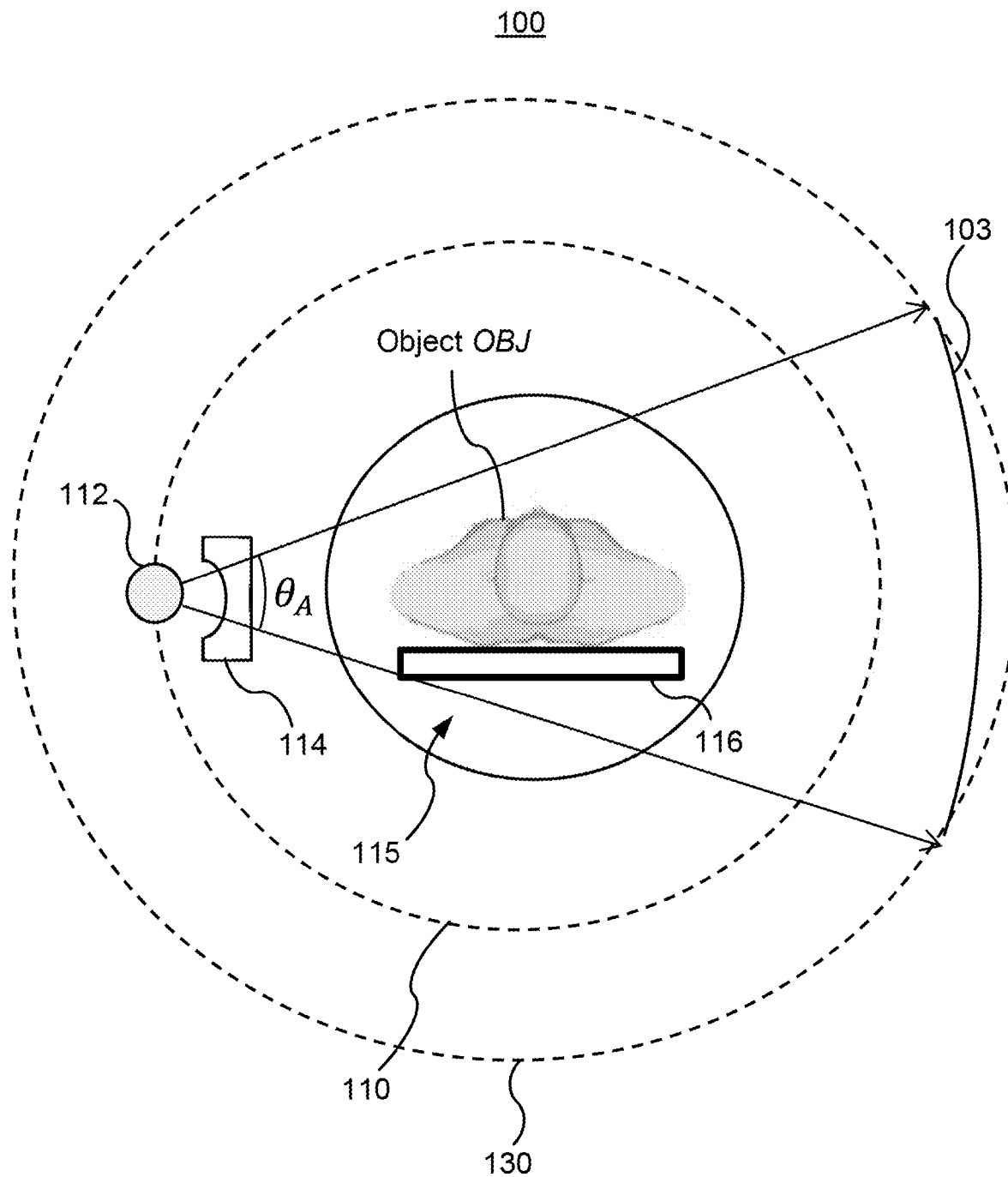
FIG. 1 shows a schematic diagram of an arrangement of an X-ray source and detector in a computed tomography (CT) scanner, according to one implementation.

In projection data acquired via kV-switching, the high-kV projection data is interleaved with the low-kV projection data because as the CT scanner progress through the series of projection angles the voltage applied across the X-ray source (e.g., X-ray tube) is switched at predefined time intervals to one or the other of the high-kV and low-kV voltage settings. Thus, for those projection angles during which the low-kV voltage settings is applied, low-kV projection data is acquired, and, in the high-kV sinogram, the projection data is missing for those projection angles. The projection images acquired in the projection data can change relatively slowly as a function of projection angle. Thus, interpolation can be used to rill in the missing high-kV projection data (i.e., the high-kV projection data for projection angles during which the low-kV voltage setting was applied). Similarly, interpolation can be used to fill in the missing low-kV projection data. This process is referred to as sinogram completion. Sinogram completion, however, is not perfect, and can lead to artifacts and degradation of the image quality. Accordingly, improved methods to perform sinogram completion, and/or to correct for the imperfections in sinogram completion are desired.

The methods and apparatus described herein overcome the above-noted artifacts and image degradation present in related approaches to sinogram completion. These deficiencies are overcome, e.g., by applying two-channel deep learning (DL) artificial neural network (ANN) that can use the additional information of the high-kV projection data to achieve better sinogram completion of the kV-switching projection data. The two-channel DL ANN can be applied to correct for imperfect sinogram completion at one or more steps along the CT image reconstruction process, including, e.g., (i) at or immediately after the sinogram completion step, (ii) at or immediately after a basis/material decomposition step, and (iii) at or immediately after an image reconstruction step. The terms "projection data" and "sinogram data" mean the same thing and are used interchangeably.

Additionally, the sinogram data can be represented in three dimensions. For example, these three dimensions can include two spatial dimensions corresponding to the two dimensions of the X-ray detector array, and the third dimension of the sinogram data can be the projection angles of the CT scan. Although these three dimensions can be accounted for using a true three dimensional convolutional neural network (CNN), two-dimensional (2D) convolutions can be computed much faster than three-dimensional convolutions. Accordingly, a 2.5 dimensional approach can be used to account for all three-dimension, by first applying 2D CNN filtering to slices parallel to a first plane, and then applying 2D CNN filtering to slices parallel to a second plane, which is orthogonal to the first plane. That is, a 3D effect can be achieved by using two 2D CNNs, rather than one 3D CNN, reducing the number of computations and time.

Further, the training and applications of the DL ANN can also be accelerated by splitting the projection data into high- and low-frequency components, which are then applied to two separate CNNs-a high-frequency CNN and a low-frequency CNN.

Moreover, in certain implementations, the high-kV projection data and the low-kV projection data can be separately applied to two separate DL ANNs. For example, the DL ANNs can be two-channel networks in which one of the channels is the projection data and the second channel is a mask indicating which pixels in the sinogram are measured data and which are filled in by the sinogram completion process. Additionally or alternatively, the mask can be used in the loss/cost function used to train the DL ANN by applying a weighting that depends on the mask.

By virtue of the above features, the methods described herein have several advantages over other dual-energy CT (DECT) systems and approaches. For example, the approaches discussed in the Background suffer from various deficiencies, including, e.g., greater hardware costs and/or degradations to the quality of the reconstructed image. For example, the methods described herein can reduce hardware cost by making high-quality images feasible using sparse-kV switching, rather than fast-kV switching. That is, the methods described herein enable improved image quality not only for fast-kV switching, but also for sparse-kV switching. By making sparse-kV switching feasible, the methods described herein can significantly reduce hardware costs because hardware for sparse-kV switching can be more cost effective.

Higher cost is a deficiency in both fast kV-switching and dual/detector-source systems. The methods described herein are compatible with sparse kV-switching, in which the kilo-voltage applied to the X-ray tube is switched infrequently (i.e., the kV switching is sparse, resulting in sparse view projection data for both low- and high-kV values). Accordingly, rather than switching between low- and high-kV values for each change of the projection angle (view), the kV-switching used herein is sparse, meaning the kV-switching is performed less frequently, such that a given kV setting is maintained as the CT scanner rotates through several projection angle before switching to the other kV setting. That is, after switching to a high kV setting the X-ray source maintains the high kV voltage while the scanner rotates through and acquires projection images at many projection angles before switching back to a low kV setting, which is then maintained through the next several projection angles, and so forth. In this way a single data acquisition system (DAS) can be used, and simpler, less expensive hardware is sufficient to switch the voltage across the X-ray tube at the slower rate and longer periods between switching the kV setting.

Further, the methods described herein overcome the deficiencies of dual-layer detectors because the two energy spectra are achieved by modulating/switching the voltage applied across the X-ray source, rather than by filtering the X-ray energies at the X-ray detector.

The methods described herein can be used with both fast-kV-switching and sparse-kV-switching dual-energy CT (DECT) systems. However, due to the cost savings for sparse-kV-switching systems, the discussion primary focuses on sparse-kV-switching systems. Sparse-kV-switching systems generate sparse-view projection data for a low- and high-energy X-ray spectra, respectively. Because the k-switching is performed less frequently than in fast k-switching, the methods described herein can be performed using a high-frequency generator (as opposed to the ultra-high frequency generator used for fast kV-switching). Further, the sparse kV-switching can be performed using a single sequential DAS (as opposed to the parallel DASs used for fast kV-switching).

One of the major challenges for the sparse kV-switching approach to DECT is that the sparse-view projection data presents challenges with respect to the image quality and material decomposition of the reconstructed images. More particularly, for sparse kV-switching projection data, it has proven difficult to develop an efficient reconstruction algorithm that is not susceptible to streak artifacts, beam hardening, and other effects that degrade the image quality. On the one hand, analytical reconstruction methods such as filtered back-projection (FBP) can be efficient, but, when applied to sparse projection data, they generate reconstructed images that suffer from streak artifacts. On the other hand, iterative reconstruction methods, when applied to sparse projection data, can reduce streak artifacts, but result in degraded spatial resolution and degraded noise texture due to the lower dose of X-rays at each kV setting. The "kV setting" is the peak kilo-voltage applied between the anode and cathode of an X-ray tube source. The term "kilo-voltage" abbreviated as kV and "peak kilo-voltage" abbreviated as kVp are used interchangeably herein.

Another challenge with sparse kV-switching projection data is that the trajectories traced by the X-rays to the detector pixels are different between the two kV settings, but sinogram-domain material decomposition requires overlapping X-rays trajectories for the two kV settings. Image-domain material decomposition, on the other hand, has its own set of difficulties, including, e.g., beam hardening corrections and spatial variations in the energy spectrum of the X-ray beam (e.g., due to different paths through a bow tie filter). Thus, the accuracy sinogram completion/correction plays a significant role in enabling accurate material decomposition in the sinogram-domain. Otherwise, imperfections in the sinogram completion process can persist and become compounded through the material decomposition and image reconstruction processes.

Referring now to the drawings, wherein like reference numerals designate identical or corresponding parts throughout the several views, FIG. 1 shows a configuration of an X-ray source and detector in computed tomography (CT) scanner having energy-integrating detectors. FIG. 1 provides a non-limiting example of relative positions among an imaged object OBJ resting on a table 116, an X-ray source 112, a collimator/filter 114, and a pixelated X-ray detector 103, which includes an array of individual detector elements (i.e., pixels).

In one implementation, the X-ray source 112, the collimator/filter 114 are fixed to a rotational component 110 that can rotate within a gantry. For example, the rotational component 110 can be an annular ring configured to rotate within a gantry while the object OBJ remains fixed in space on the table 116, or, alternatively, in a helical scan, the table can be translated along the bore of the gantry while the X-ray source 112 and the X-ray detector 103 are rotated around the bore of the gantry. The gantry of the CT scanner also includes an open aperture 115 within the bore, which can be centered at the iso-center of the rotational component 110. The open aperture 115 enables the object OBJ to be placed in a projection plane of the X-rays from the X-ray source. In certain implementations, the X-ray detector 103 is fixedly connected to another rotational component 130 that is rotatably connected to the gantry. In a rotate/rotate configuration, the rotational component 110 and the rotational component 130 can rotate in unison, maintaining the X-ray detector 103 diametrical opposed to the X-ray source 112 to obtain projection data of the object OBJ/at a progression of projection angles (i.e., views). Sinograms are created by arranging the projection data with projection angles arranged along one axis and the spatial dimensions of the projection data arranged along the other axes. The projection data (sinograms) can be used to reconstruct a cross-sectional image of the object OBJ.

In spectral CT, projection data having multiple energy components is used to represent projective measurements of the object OBJ. These projective measurements are made at a series of angles (views), enabling conventional CT image reconstruction methods similar to non-spectral CT. However, unlike non-spectral CT, spectral CT generates additional information (i.e., spectral attenuation information)

enabling a decomposition of the projective measurements into material components. Setting aside k-edge methods, the number of materials is usually two, based on the unique spectral signatures of X-ray attenuation due to Compton scattering and photoelectric attenuation, respectively. That is, the spectral differences between the X-ray attenuation for two material components arise from the different ratios of Compton scattering to photoelectric attenuation they exhibit (e.g., the X-ray attenuation due to a high-Z material like iodine is comprised of a different ratio of Compton scattering to photoelectric attenuation than a low-Z material like water).

Mapping the projection data from the spectral domain to the material domain can be performed either in the sinogram-domain (i.e., before the image reconstruction process) or in the image-domain (i.e., after the image reconstruction process). However, to be performed in the sinogram (projection) domain, the projection data should include identical (or nearly identical) X-ray trajectories for each of the dual-energy components. In kV-switching, differences between X-ray trajectories arise from the fact that the projection views at which the high-kV setting is used the low-kV projection data is missing, and vice versa.

The attenuation of X-rays in biological materials is dominated by two physical processes (i.e., photoelectric absorption and Compton scattering). Thus, the attenuation coefficient as a function of energy can be approximated by the decomposition $$\mu(E,x,y) = \mu_{PE}(E,x,y) + \mu_C(E,x,y),$$

wherein $\mu_{PE}(E,x,y)$ is the photoelectric attenuation and $\mu_C(E,x,y)$ is the Compton attenuation. Alternatively, this attenuation coefficient can be rearranged into a decomposition of a high-Z material (i.e., material 1) and a low-Z material (i.e., material 2) to become $$\mu(E,x,y) = \mu_1(E)c_1(x,y) + \mu_2(E)c_2(x,y),$$

wherein $c_1(x,y)$ and $c_2(x,y)$ are, respectively correspond to a first and second material component. Material decomposition is the process of solving from the $c_1(x,y)$ and $c_2(x,y)$ that best approximate with measured/reconstructed attenuation spectra.

Figure 2A:
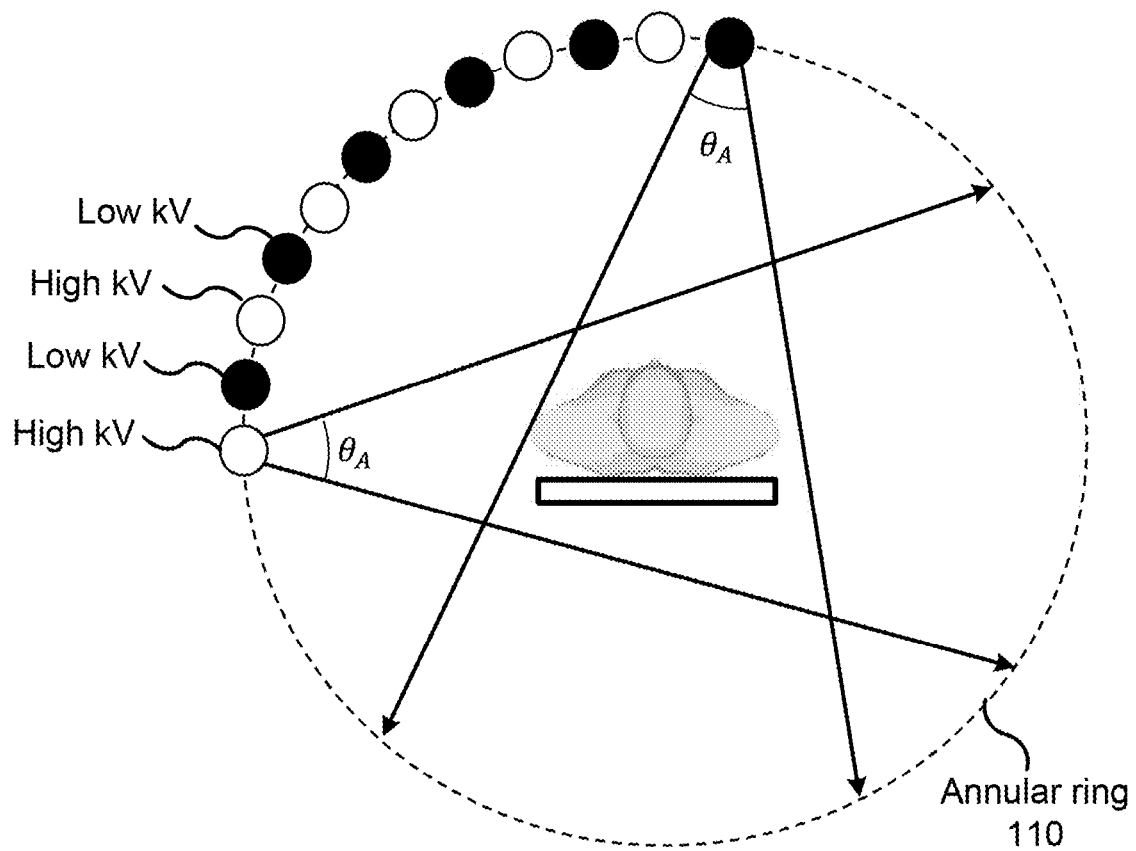
FIG. 2A shows an example of projection angles/views of an X-ray source for fast kV-switching, according to one implementation.
Figure 2B:
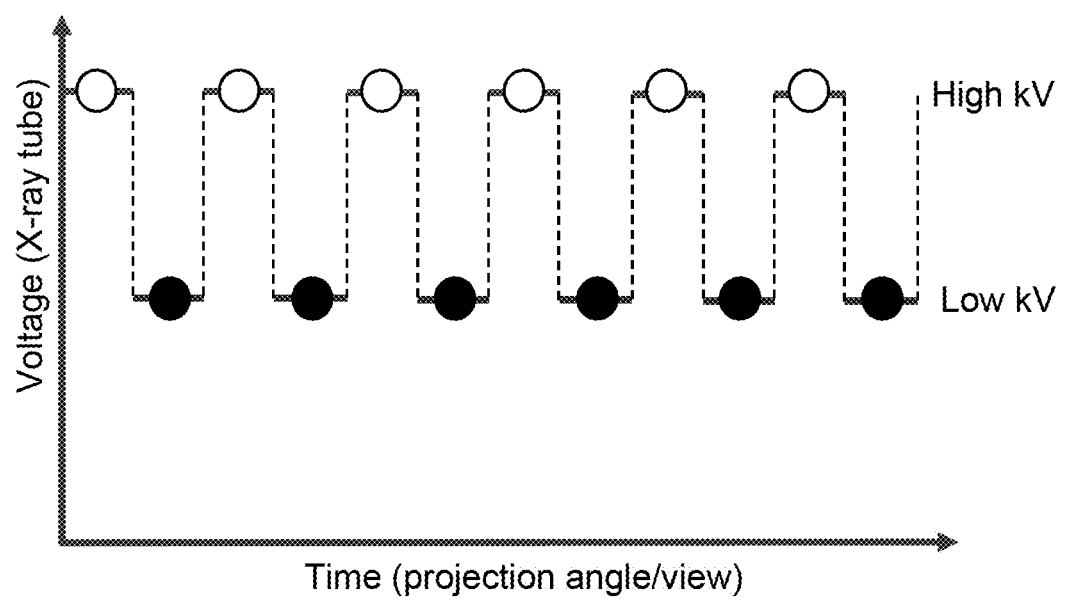
FIG. 2B shows an example of kilo-voltage peak values as a function of time for fast kV-switching, according to one implementation.

FIGS. 2A and 2B show diagrams of an implementation of fast kV-switching. The kV setting on the X-ray tube is changed for each projection angle. In FIG. 2A, the locations of the X-ray source for acquisitions of a projection image using a high-kV (low-kV) setting are indicated by the white (black) circles. In FIG. 2B, the voltage applied to the X-ray tube is shown as a function of time, with the time and voltage for projection images acquired at the high-kV (low-kV) setting indicated by the white (black) circles.

Figure 3A:
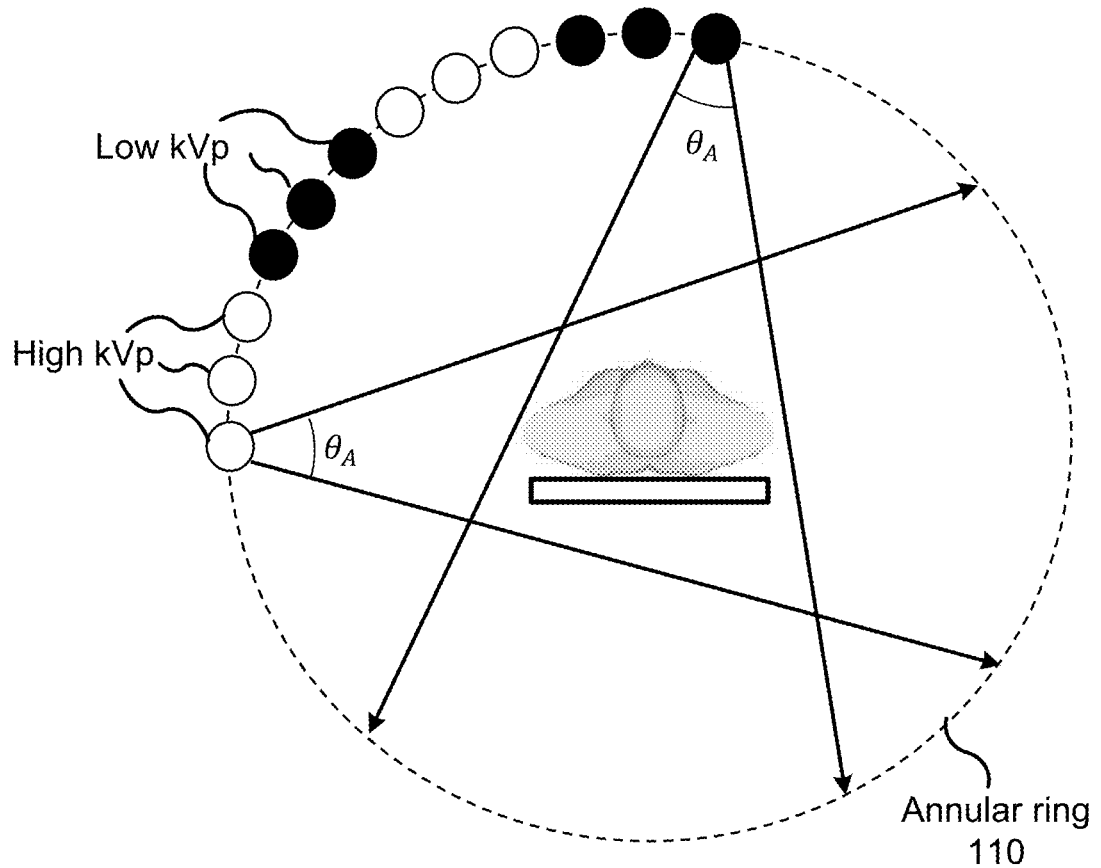
FIG. 3A shows an example of projection angles/views of an X-ray source for sparse kV-switching, according to one implementation.
Figure 3B:
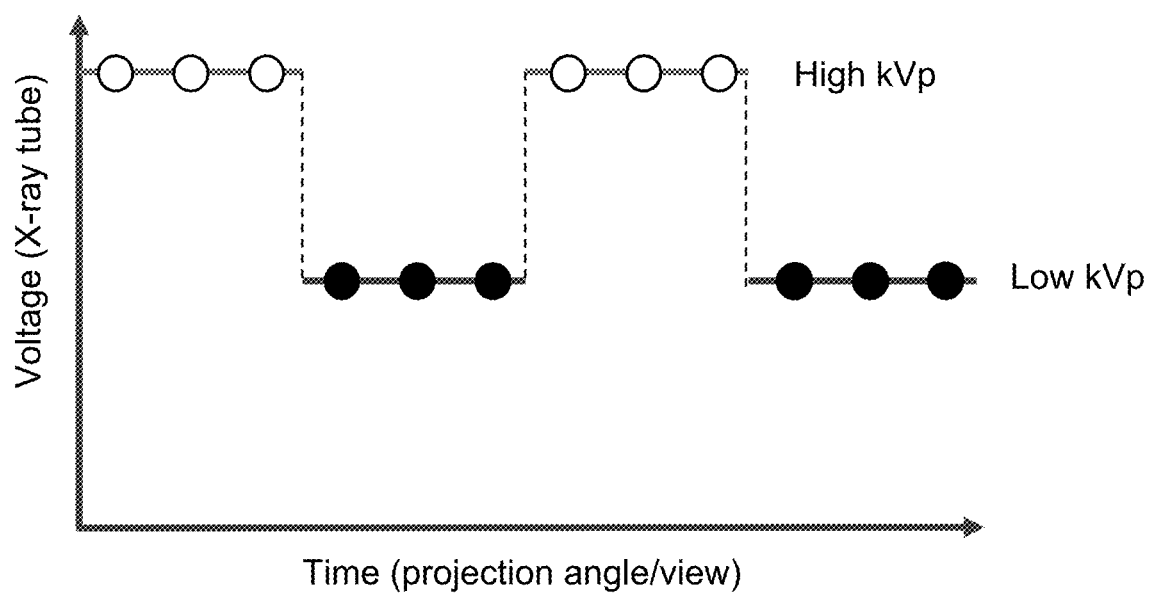
FIG. 3B shows an example of kilo-voltage peak values as a function of time for sparse kV-switching, according to one implementation.

FIGS. 3A and 3B show diagrams of an implementation of sparse kV-switching. The kV setting on the X-ray tube is changed only after a succession of N projection images at different projection angles have been acquired, where N is a number greater than one. In FIG. 3A, the locations of the X-ray source for acquisitions of a projection image using a high-kV (low-kV) setting are indicated by the white (black) circles. In FIG. 3B, the voltage applied to the X-ray tube is shown as a function of time, with the time and voltage for projection images acquired at the high-kV (low-kV) setting indicated by the white (black) circles.

In the non-limiting example shown in FIGS. 3A and 3B, N is three, but N can be any integer two or greater. Further, the number of successive projection images acquired at a given kV setting does not need to be constant throughout a CT scan, and different interval lengths can be applied for different kV settings (e.g., within a given CT scan, more projection images can be acquired at a high-kV setting than at a low-kV setting or vice versa).

Figure 4:
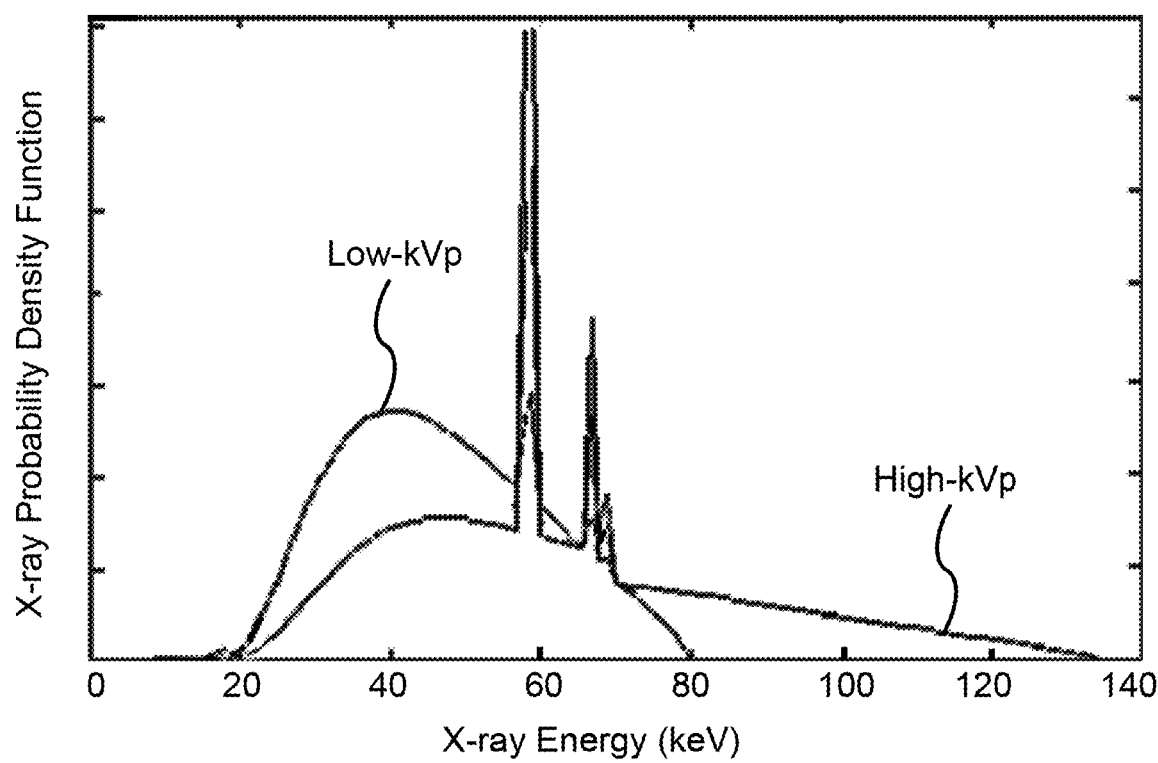
FIG. 4 shows a plot of a probability density function for an energy spectra of X-rays emitted at low- and high-kV voltage settings, according to one implementation.

The method of sparse kV-switching is illustrated herein using the non-limiting example of a low-kV setting of 80 kV and a high-kV setting of 135 kV. For an X-ray tube, the X-ray spectrum is mainly controlled by the voltage (kV) applied between the anode and cathode to accelerate the electrons before the electrons are suddenly stopped by colliding with the cathode, converting the kinetic energy of the electron into X-rays via a Bremsstrahlung radiation mechanism. By this process, different X-ray spectra can be produced by changing the voltage applied across of the X-ray tube. FIG. 4 shows the probability distribution of the X-ray energy produced with a low-kV setting of 80 kV and a high-kV setting of 135 kV, respectively.

The methods described herein are illustrated using the non-limiting example in which two voltages are applied to the X-ray source to generate two different X-ray spectra. However, the methods described herein are also applicable and include the use of three or more voltage settings applied to the X-ray source to generate three or more different X-ray spectra. For example, the kV-switching can be performed using high-kV, and middle-kV, and low-kV settings, in this case, for example, a three-channel neural network can be used in place of the two-channel neural network described below for the case illustrated using high-kV and low-kV settings. Using three or more X-ray spectra has the advantage of providing additional information for material decomposition. Accordingly, an implementation with kV-switching in which three or more voltage settings applied to the X-ray source does not depart from the spirit of the methods described herein.

Figure 5A:
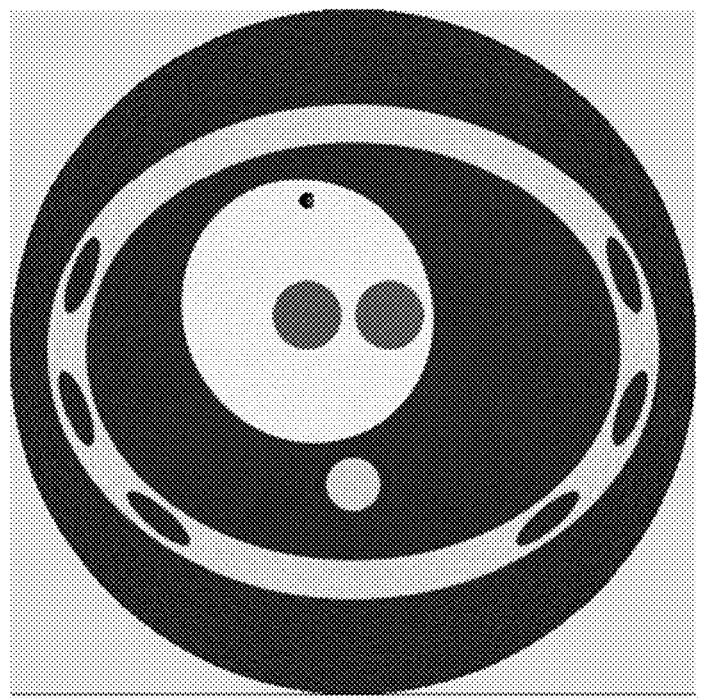
FIG. 5A shows a radiodensity cross-section of a first material component (e.g., water) for a phantom, according to one implementation.
Figure 5B:
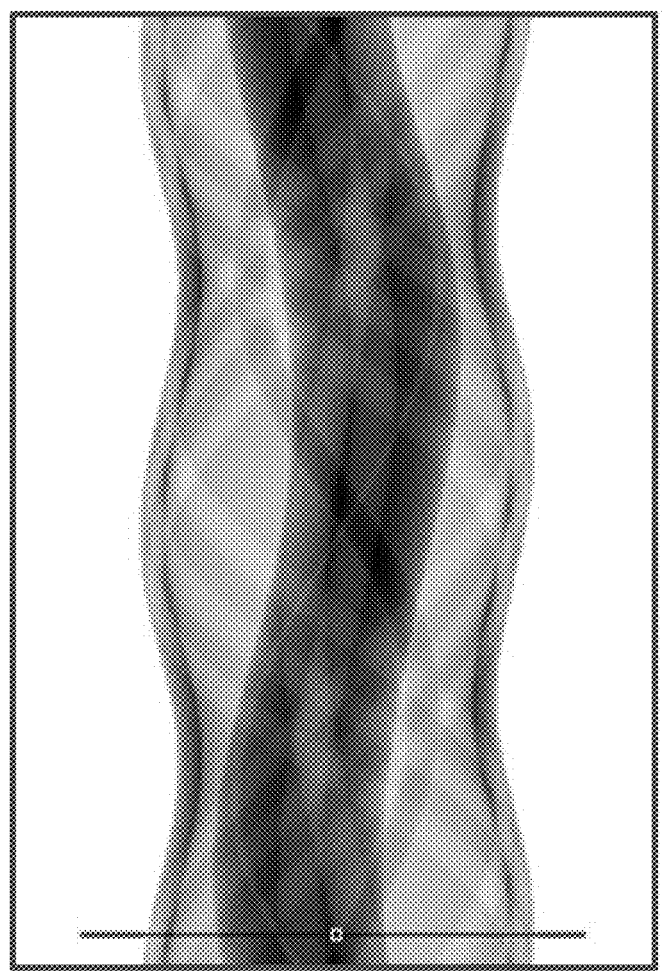
FIG. 5B shows a sinogram of the material component in FIG. 5A of the phantom, according to one implementation.
Figure 6A:
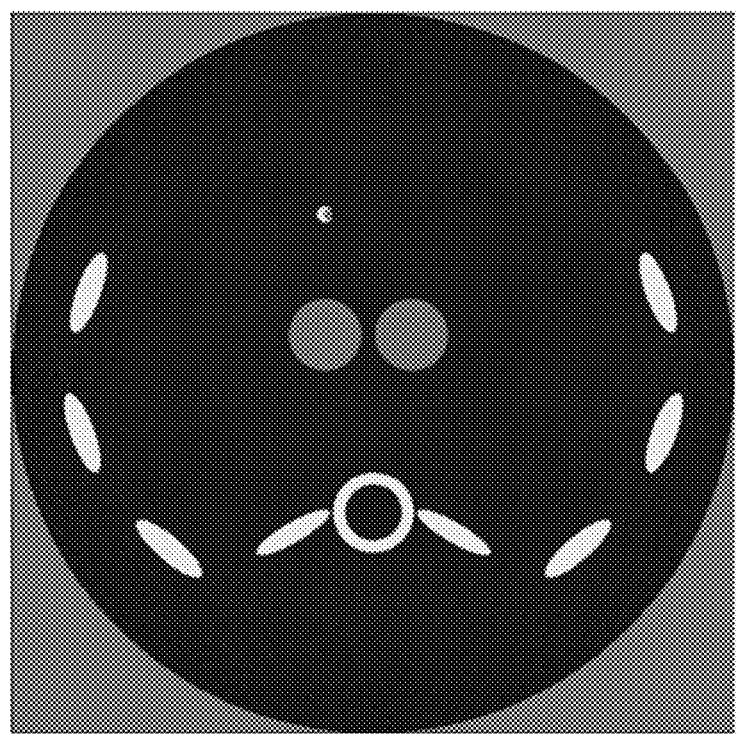
FIG. 6A shows a radiodensity cross-section of a second material component (e.g., bone) for the phantom, according to one implementation.
Figure 6B:
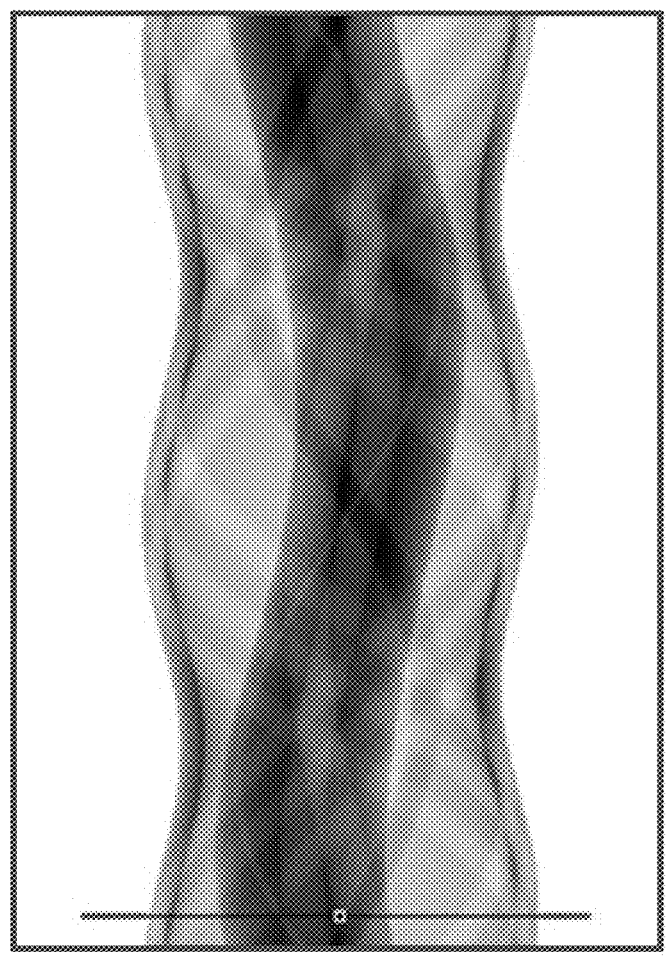
FIG. 6B shows a sinogram of the material component in FIG. 6A of the phantom, according to one implementation.

FIGS. 5A and 6A show cross-sectional views for two material components of a phantom that is used as a non-limiting example. In this non-limiting example, the two material components are water and bone. FIGS. 5B and 6B show the water and bone sinograms corresponding to the cross-sections shown FIGS. 5A and 6A. These are the complete sinograms (i.e., no projection data is missing). The spatial dimension is represented along the horizontal axis and the projection angle is represented along the vertical axis. These material-component sinograms can be obtained by decomposing the sinograms shown in FIGS. 7A and 7B, which correspond to kV settings of 80 kV and 135 kV, respectively.

In contrast to the complete sinograms shown in FIGS. 7A and 7B, FIGS. 7C and 7D show interleaved sparse-view projection data in which, for each projection angle, the projection data has been acquired using either a kV setting of 80 kV or a kV setting of 135 kV. A sinogram completion method (e.g., interpolation or inpainting) can be used to fill in the attenuation values at the missing projection angles for each of the 80 kV and 135 kV sinograms.

Sparse-view projection data can be approximated from the complete sinograms by designating alternate intervals of the projection angle as corresponding either to a high- or a low-kV setting, and then deleting the low-kV sinogram values for those intervals in which the high-kV setting is applied (and vice versa). In transition regions from the high-kV setting to the low-kV setting (and vice versa), a superposition of the high-kV and low-kV sinograms can be used to approximate transient effects of the switching process.

Figure 7D:
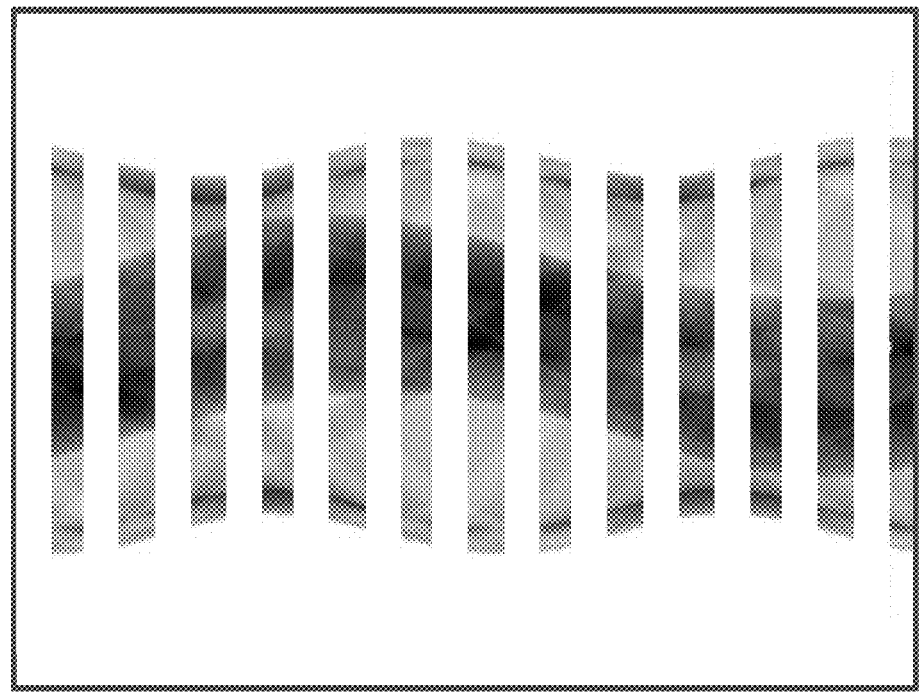
FIG. 7D shows a sparse-view sinogram corresponding to the sinogram shown in FIG. 7B, according to one implementation.
Figure 7C:
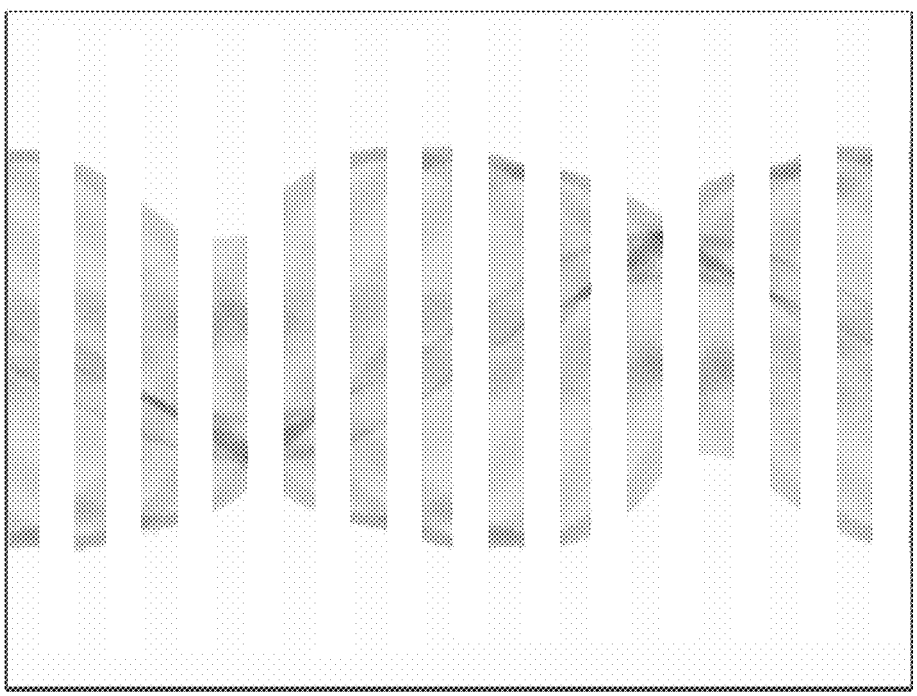
FIG. 7C shows a sparse-view sinogram corresponding to the sinogram shown in FIG. 7A, according to one implementation.
Figure 8A:
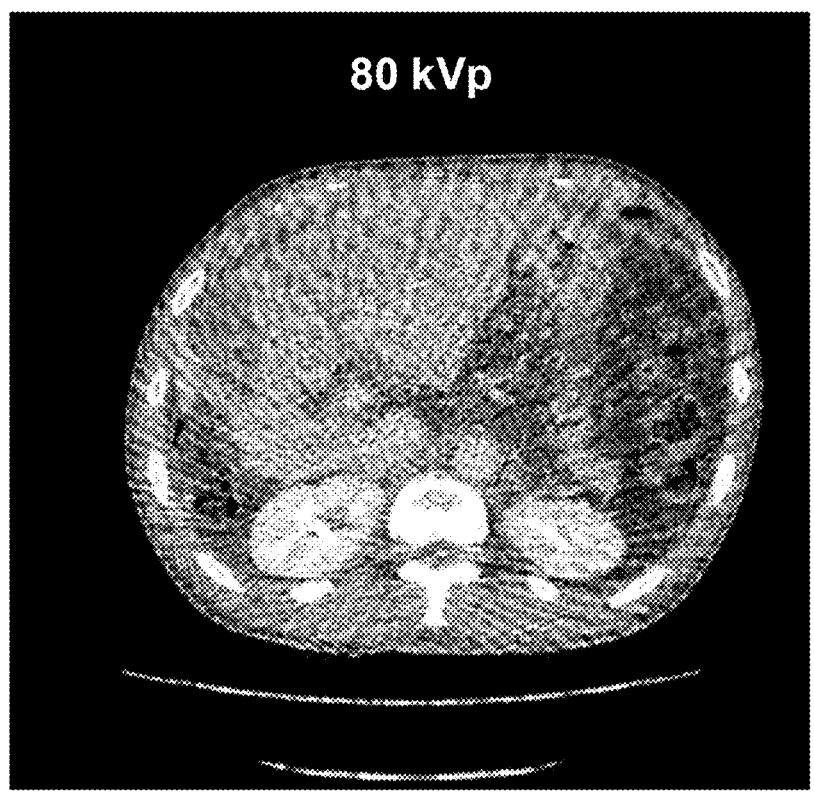
FIG. 8A shows an image reconstructed using an adaptive iterative dose reduction (AIDR) three-dimensional (3D) reconstruction method, the image being reconstructed from sparse kV-switching projection data for a low-kV value of 80 kVp, according to one implementation.
Figure 8B:
FIG. 8B shows an image reconstructed using an AIDR-3D method, the image being reconstructed from sparse kV-switching projection data for a high-kV value of 135 kVp, according to one implementation.
Figure 8C:
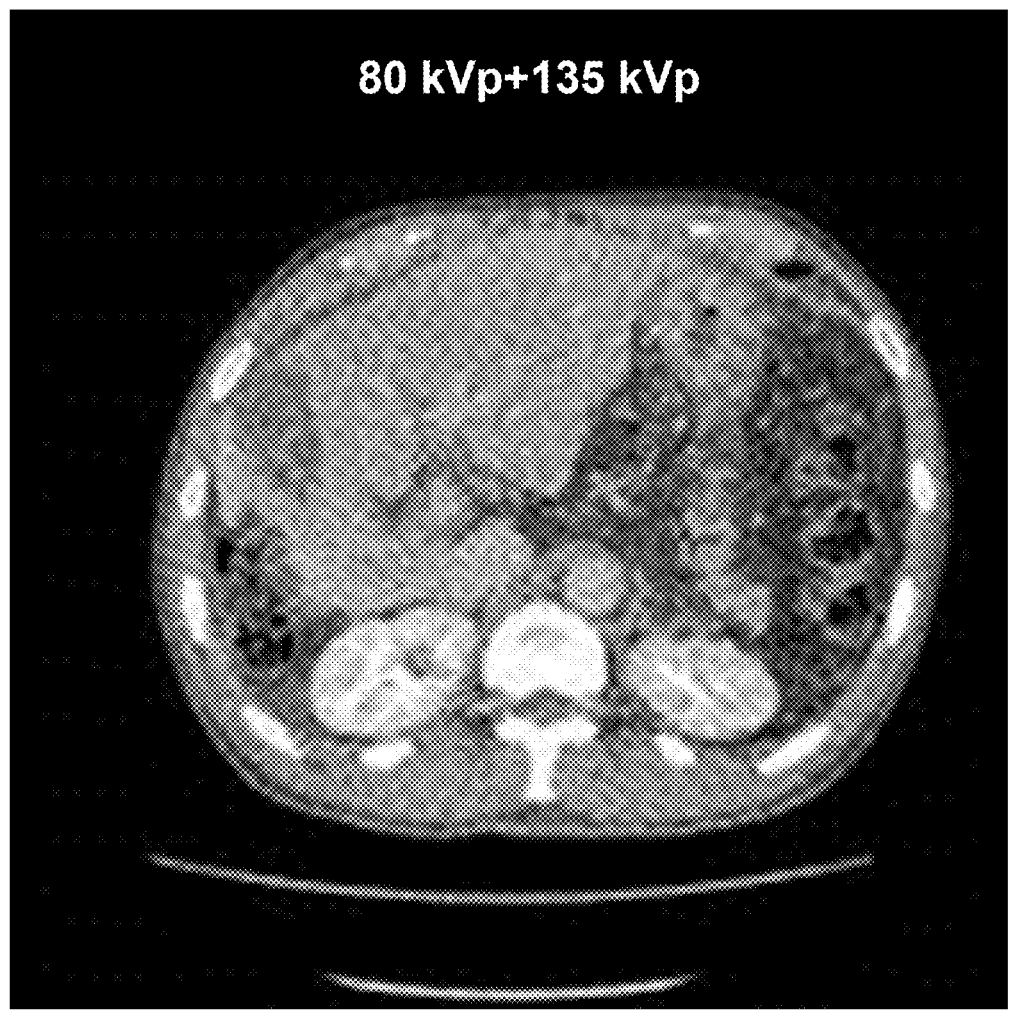
FIG. 8C shows a sum of the images in FIGS. 5A and 5B, according to one implementation.

As discussed above, a challenge of image reconstruction using projection data acquired using sparse kV-switching is that the image quality tends to be degraded due to streak artifacts. For example, FIGS. 8A and 8B show examples of reconstructed images generated using FBP reconstruction with sparse k-switching projection data for 80 kV and 135 kV, respectively. The streak artifacts are clearly evident. Further, close inspection reveals that the streak artifacts tend to be complementary. That is, a bright streak in the 80 kV image corresponds to a dark streak in the 135 kV image, and vice versa. To illustrate this, FIG. 8C shows a sum of the 80 kV image with the 135 kV image. To a significant degree the bright streak artifacts in the 80 kV image counteract the dark streak artifacts in the 135 kV image. These streak artifacts can be understood as arising from the fact that the projection angles for the 80 kV and 135 kV projection data are complementary/interleaved, as shown in FIGS. 7C and 7D. For example, the projection angles for which the CT scanner is set to the high-kV setting is the complement of the projection angles for which the CT scanner is set to the low-kV setting. Thus, the information from the two images at the respective high- and low-kV settings are complementary.

The methods described herein use a DI-ANN to learn how to use the combined information from the respective low- and high-kV projection data to perform sinogram completion and/or correct for the residual errors resulting from imperfect sinogram completion.

Figure 9A:
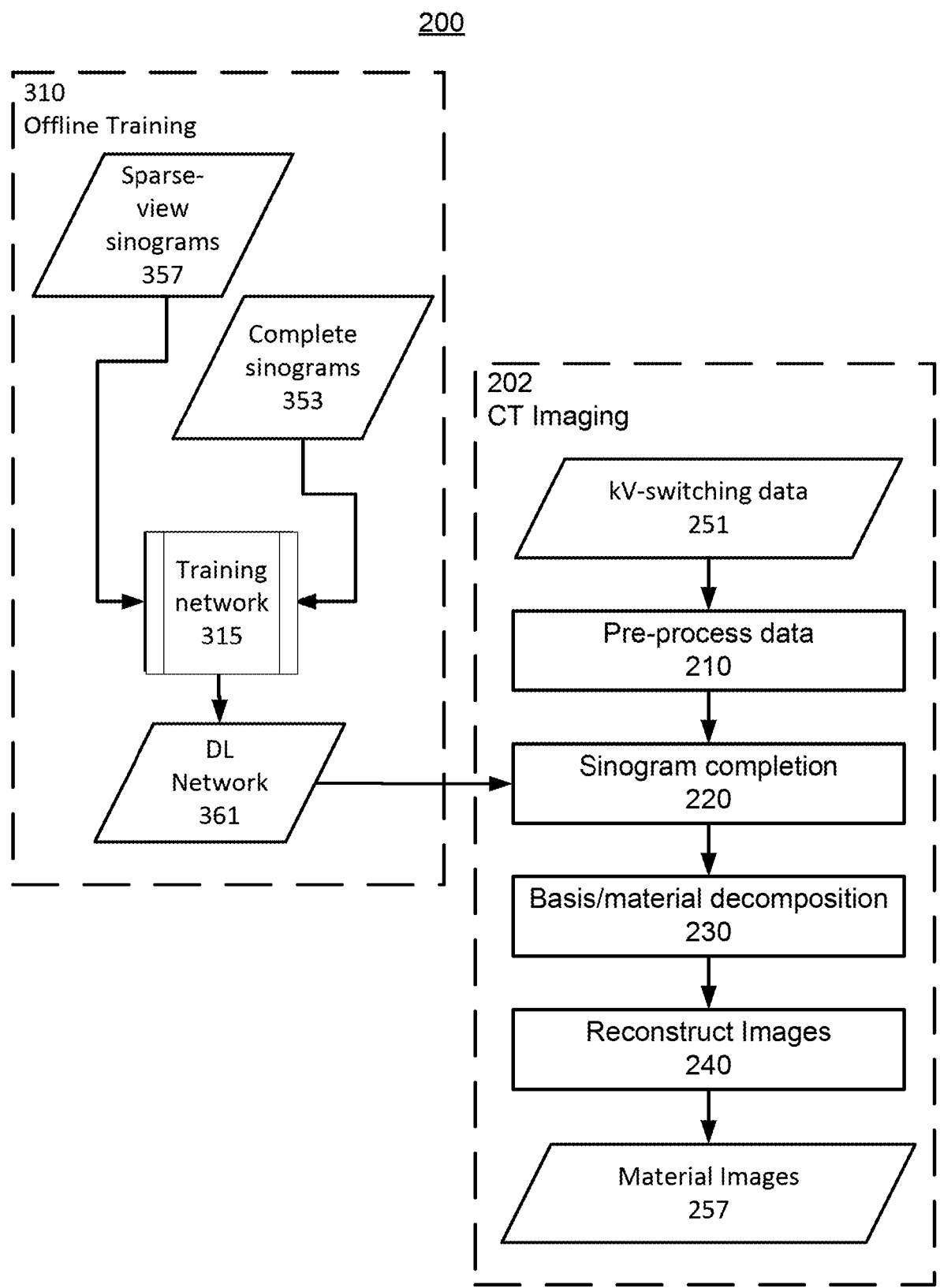
FIG. 9A shows an example of a flow diagram for training and using a deep learning (DL) artificial neural network (ANN) to perform sinogram completion of kV-switching projection data (e.g., sparse-view kV-switching projection data), according to one implementation.

FIG. 9A shows a flow diagram of a method 200 for sparse kV-switching CT image reconstruction that includes a process 310 of training a DL ANN 361, and includes a process 202 of using the trained artifact-correction network 361 to correct sparse-view projection data 251 to ultimately generate high-quality material-basis images 257.

In process 310, a loss function is used to iteratively adjust/optimize parameters of the DL-ANN network 361 (e.g., the parameters of the DL-ANN network 361 can include weighting coefficients connecting network layers, and activation functions/potentials of nodes within the layers). The optimization of the network parameters continues until stopping criteria are satisfied (e.g., convergence of the network coefficients/parameters to a predefined threshold) to generate the trained network 361. The loss function compares a complete sinogram 353 (e.g., full-scan acquired at each of the respective kV settings) to a result output by the network when sparse-view acquisition 357 (e.g., sparse k-switching images) are applied to a current version of the DL-ANN network 361. The sparse-view sinograms 357 can be sinograms like those shown in FIGS. 7C and 7D, in which intervals of the projection angle have no attenuation values. Alternatively, the sparse-view sinograms 357 can be sinograms for which an imperfect sinogram completion method (e.g., interpolation or inpainting) has already been applied prior to the sparse-view sinograms 357 being applied to the DL-ANN network 361. In the first case, the DL-ANN network 361 is trained to fill in the missing sinogram data, and, in the second case, the DL-ANN network 361 is trained to correct for the imperfections of the imperfect sinogram completion method.

Figure 7B:
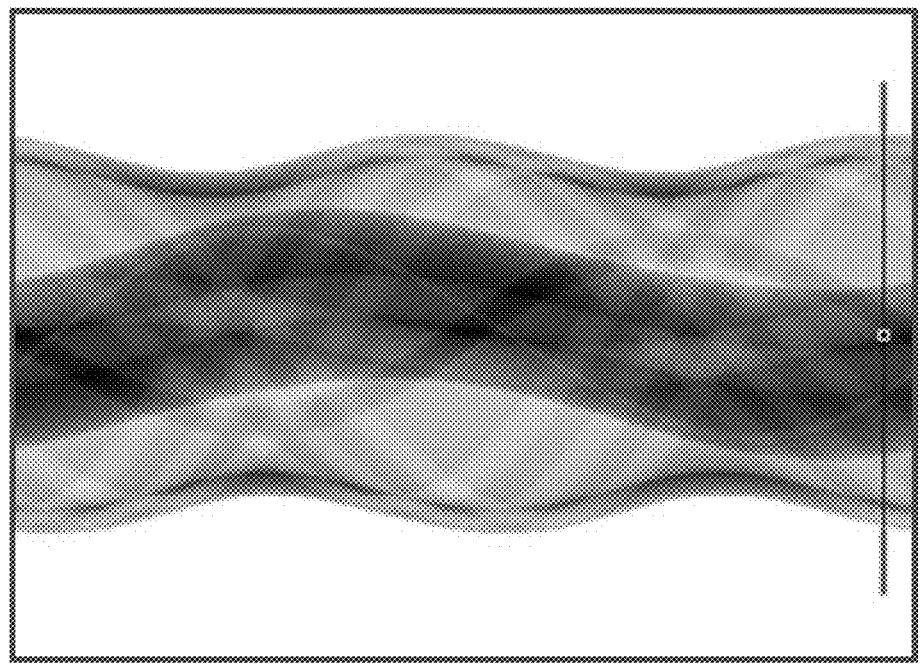
FIG. 7B shows a sinogram corresponding to an X-ray energy spectrum for a 135 kV setting on the X-ray tube, according to one implementation.
Figure 7A:
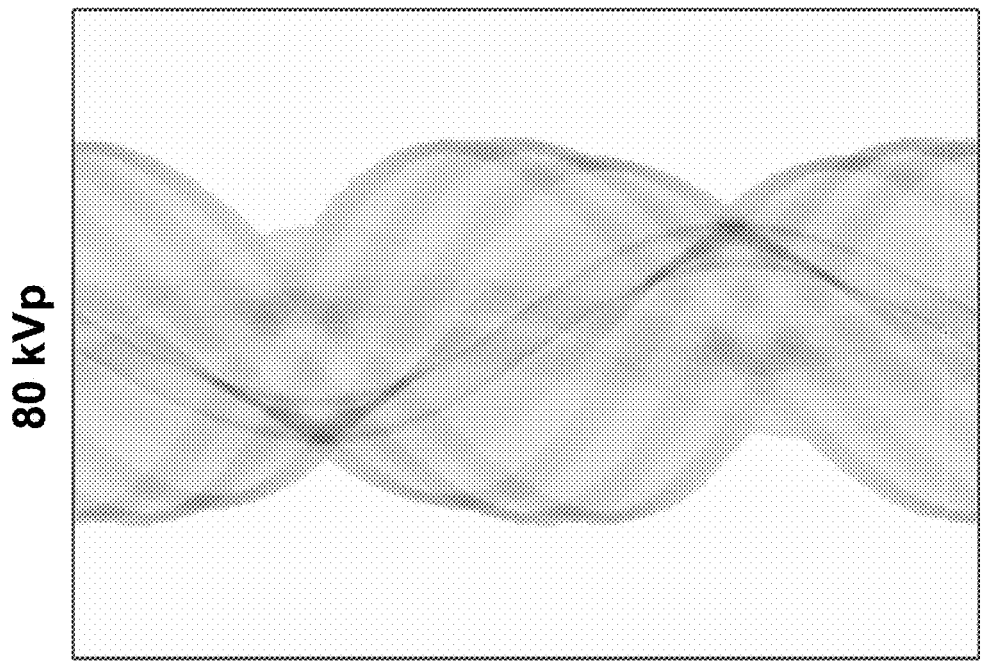
FIG. 7A shows a sinogram corresponding to an X-ray energy spectrum for an 80 kV setting on an X-ray tube, according to one implementation.

The DL-ANN network 361 can be a two channel network in which the target data (i.e., complete sinograms 353) includes a pair of complete sinograms corresponding respectively to the two kV settings (i.e., the high-kV setting and the low-kV setting, as shown in FIGS. 7A and 7B). The input data (i.e., sparse-view sinograms 357) also includes a pair of sinograms corresponding respectively to the two kV settings, but the input data, which is applied to the DL-ANN network 361 to generate the result that is compared to the target data, is either sparse-view sinograms (as shown in FIGS. 7C and 7D) or a result of performing an initial-but-imperfect sinogram completion method on the sparse-view sinograms 357. In general the training dataset used to perform process 310 will include a large number of sets of input sinograms paired with respective target sinograms. The complete sinograms can be referred to as the "target" or "label," and the sparse-view sinograms are referred to as the "input" The training data can include a large set of corresponding targets and inputs. In certain implementations, the offline training can be performed in advance of a given CT scan (e.g., when a CT scanner is initially installed and calibrated), and the trained DL-ANN network 361 can be stored in memory until a CT scan is acquired and the image reconstruction is performed in step 220. In general, the sparse-view sinograms 357 are prepared in a similar manner to or consistent with how the kV-switching projection data 251 is acquired and then pre-processed in step 210 of process 202. In this way, the DL-ANN network 361 is trained to correct the particular artifacts and deficiencies arising in the pre-processed sinograms resulting from step 210.

In FIG. 9A, CT projection data 251 that have been generated using either fast or sparse kV-switching are processed using steps 210, 220, 230 and 240 to generate high-quality basis/material images 257. The basis/material images 257 are often material-component images (e.g., the material components can be bone and water). However, other bases can also be used in place of material-components bases. For example, the basis decomposition can decompose the dual energy images into a Compton-scattering-attenuation basis and a photoelectric-effect-attenuation basis. Although the basis decomposition is more general than just material decomposition, the non-limiting example of material decomposition is often used herein to illustrate various implementations of process 202.

In certain implementations, the CT projection data 251 can be projection data acquired from a CT scan that are pre-processed at step 210 (e.g., signal preconditioning, calibration corrections, baseline corrections, beam hardening corrections, etc.). In certain implementations, the pre-processing performed at step 210 includes initial sinogram completion (e.g., interpolation). The projection data 251 can be a sinogram that is corrected using various calibration and geometric factors. For example, the pre-processing can include corrections such as baseline subtraction for a detector offset, corrections for variations in amplifier gain and quantum efficiency among the detectors, corrections for a non-linear detector response as a function of X-ray flux, etc. Further, these corrections can be based on calibration data, empirical derived parameters, and a priori known parameters.

In step 220 of process 202, the sinograms resulting from step 210 are applied to the trained DL-ANN network 361 from process 315. In certain implementations, the DL-ANN network 361 from process 315 performs sinogram completion, and, in other implementations, the DL-ANN network 361 from process 315 corrects for imperfections in an initial sinogram completion performed at step 210.

As discussed above, to take advantage of the complementary information between the high- and low-kV sparse-view sinograms, the DL-ANN network 361 can be a two-channel network. Since low- and high-energy data are complementary to each other, using a two-channel network that analyses the mutual, complementary information from both channels provides significant benefit over a one-channel network that considers each energy component (kV setting) separately.

Accordingly, in step 220 of process 202, the network 361 can be a two-channel network that utilizes the complementary information between the low- and high-energy projection data. In certain implementations, the training performed in process 315 uses input images that are generated using the same pre-processing techniques as in step 210.

In step 230 of process 202, basis/material decomposition is performed on the sinograms resulting from step 220. In general, any basis/material decomposition method can be used to generate basis/material-component sinograms.

In step 240 of process 202, the image reconstruction can be performed on the basis/material-component sinograms using a back-projection method, a filtered back-projection method, a Fourier-transform-based image reconstruction method, an iterative image reconstruction method, a matrix-inversion image reconstruction method, a statistical image reconstruction method, or other reconstruction method as would be understood as a person of ordinary skill in the art. For example, the reconstruction method can use a helical reconstruction technique, a cone-beam reconstruction technique, a Feldkamp algorithm, a FBP reconstruction method, and an adaptive iterative dose reduction (AIDR) three-dimensional (3D) reconstruction method with noise reduction in one or both of the image and sinogram domains. The reconstruction can include denoising, corrections to minimize photon starvation in high attenuation regions, corrections to mitigate quantum noise, edge-preservation/enhancement corrections, and filtering (e.g., linear and non-linear filtering and denoising).

Figure 9B:
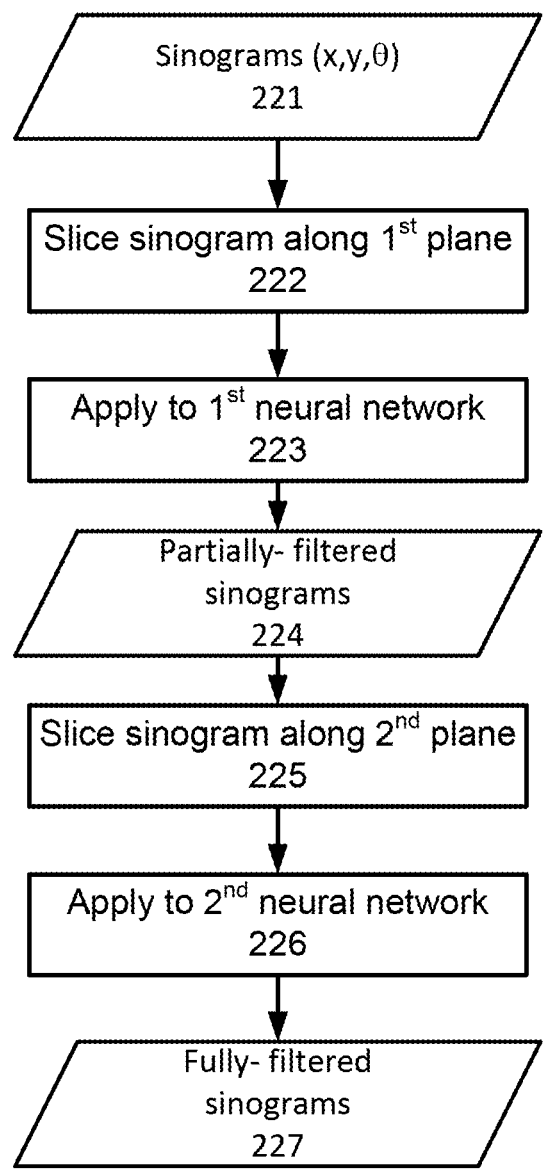
FIG. 9B shows a flow diagram of a 2.5-dimensional filtering approach that uses two 2-dimensional neural networks to perform three-dimensional sinogram completion/correction, according to one implementation.
Figure 9C:
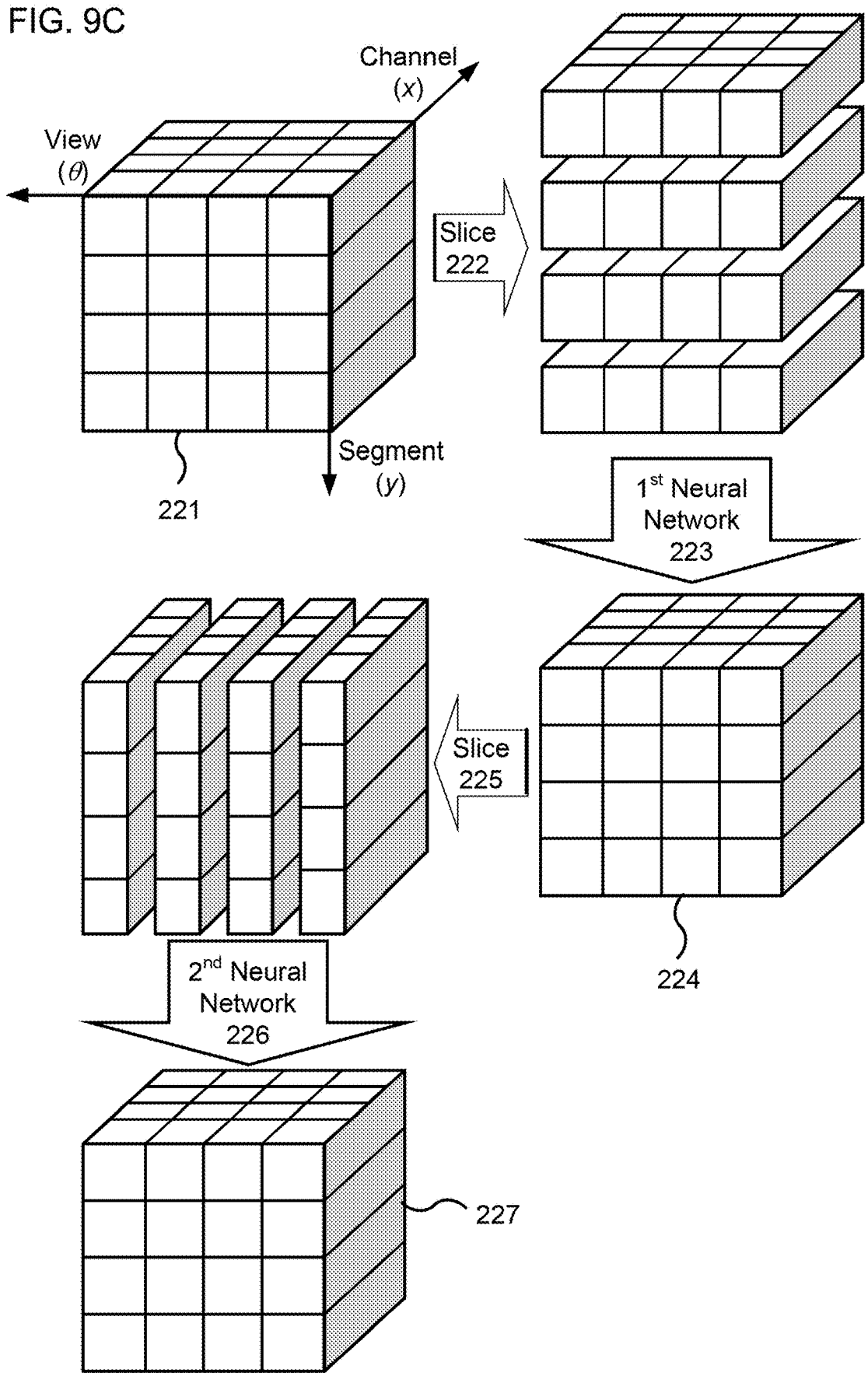
FIG. 9C shows another flow diagram of the 2.5-dimensional approach to perform three-dimensional sinogram completion, according to one implementation.

FIGS. 9B and 9C show flow diagrams for step 220 to apply the pre-processed sinograms 221 from step 210 to the trained DL-ANN network 361, in FIGS. 9B and 9C, the DL-ANN network 361 has been split into two networks (i.e., a first neural network and a second neural network) that are used in series to process the sinograms. The sinograms have three dimensions-two spatial dimensions (x,y) corresponding to the dimensions of the detector array, and a third dimension for the projection angle θ at which the projection data is acquired.

Using a 3D sinogram block is favorable to complete the missing kV measurement due to the feature continuity in all three directions (view, segment, channel). However, training and using 3D sinogram blocks can be time consuming due to increased feature dimensions, resulting in slow convergence during the training step and time-consuming computations when the kV-switching sinograms are applied in step 220. Thus, step 220 can be split into two steps, each step using a different 2D network corresponding to different pairs of the three dimensions of the sinogram. This two-step application of a neural network, which can be referred to a 2.5-dimensional (2.5D) approach, can decrease the computational burden relative to the full 3D approach, while still exploiting the information in all three dimensions of the sinograms.

The 2.5D approach begins with partitioning the dual-kV sinograms into 2D slices (e.g., view-channel slices) of the sinograms, and a first neural network is trained to achieve optimal sinogram-completion using these first 2D slices, and generate an intermediary sinogram, which is partially corrected/filtered. This partially corrected/filtered sinogram is then sliced along another plane to generate a second set of 2D slices (e.g., channel-segment slices), which are then applied to a second network that has been trained to further correct/perform sinogram completion.

In step 222, the high- and low-kV sinograms are sliced into 2D planes parallel to a first plane. For example, in FIG. 9C the 3D sinograms are sliced/partitioned into view-channel planes. Herein, the spatial dimension x is also referred to as the channel dimension, and the spatial dimension y is also referred to as the segment dimension.

In step 223, the first neural network, which is a 2D convolutional neural network (CNN), is applied to each of the slices from step 222, and the slices are recombined to generate partially-filtered sinograms 224 for the high- and low-kV settings. The first neural network can be a two-channel network (i.e., one channel corresponding to the low-kV sinogram and the other channel corresponding to the high-kV sinogram) to take advantage of the complementary information provided by the two channels.

In step 225, the partially-filtered sinograms 224 are sliced into 2D planes parallel to a second plane. For example, in FIG. 9C the partially-filtered sinograms 224 are sliced/partitioned parallel to the channel-segment plane.

In step 226, the second neural network, which is a 2D CNN, is applied to each of the slices from step 225, and the slices are recombined to generate fully-filtered sinograms 227 for the high- and low-kV settings. The second neural network can be a two-channel network (i.e., one channel corresponding to the low-kV sinogram and the other channel corresponding to the high-kV sinogram) to take advantage of the complementary information provided by the two channels.

Because 2D convolutions can be performed much faster than 3D convolutions, two 2D CNNs can be performed faster than one 3D CNN. Further, during training, each of the two 2D CNNs can separately converge much faster than a 3D CNN. For training, the complete sinograms can be used as the target data for training each of the first and second 2D CNNs.

The choice of the first slices being in the view-channel plane and the second slices being in the channel-segment plane is provided as a non-limiting example for purposes of explanation. In general, any two planes can be chosen for the first and second slices.

Figure 9D:
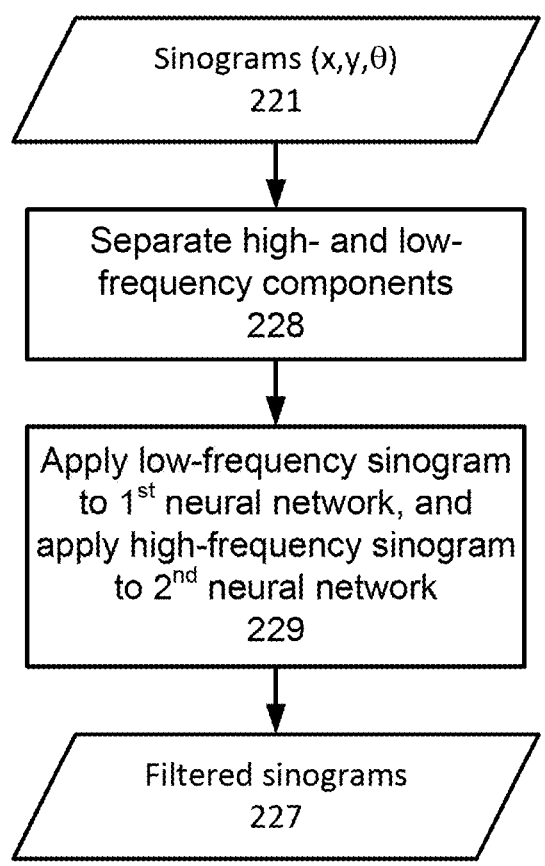
FIG. 9D shows a flow diagram of a frequency-splitting approach to ANN-based sinogram completion, according to one implementation.

FIG. 9D shows a flow diagram of step 220 in which the input sinograms are split into low-frequency and high-frequency components. In training a neural network, low-frequency components tend to converge more quickly than high-frequency components. Further, the low-frequency components can be downsampled to a lower resolution, accelerating the calculations, and the perception fields for convolutional layers for the low-frequency components can differ from (e.g., be larger than) the perception fields for a high-frequency neural network. Accordingly, there are benefits to separating the sinograms into high- and low-frequency components and training a low-frequency component neural network for use with the low-frequency components of the sinograms.

Accordingly, in certain implementations, performance/convergence and efficiency of the network can be improved by splitting the network into a low frequency component and a high frequency component. Then, deep learning is conducted by separately training the two separate networks for different frequency components. For example, this split-frequency approach can be implemented by, first, interpolating each of the high- and low-kV sinograms separately to fill in and create fully sampled dual-kV sinograms (e.g., sinogram completion at step 210). Second, a Gaussian filter is applied to each kV sinogram to obtain the low frequency component, and the high frequency component is subsequently obtained as the difference between the fully sampled dual-kV sinogram and its low frequency component. Third, two separate deep learning networks are trained: (i) a low-frequency neural network for the two low-frequency component sinograms and (ii) a high-frequency neural network for the two high-frequency component sinograms. Finally, in the dual kV sinogram completion process in step 220, the sparse dual kV sinograms are divided into low- and high-frequency components, and then applied to the respective low- and high-frequency neural networks. The low- and high-frequency results from the respective neural networks are then recombined to generate the filtered sinograms 227 resulting from the step 220.

In step 228, each of the pre-processed sinograms 221 is decomposed into a high- and low-frequency component. As discussed above, in certain implementations, this frequency splitting can be performed by low-pass filtering the pre-processed sinograms 221 to obtain the low-frequency component sinogram, and then subtracting the low-frequency component sinogram from the corresponding pre-processed sinogram 221 to obtain the high-frequency component sinogram. Alternatively, in certain other implementations, the frequency splitting can be performed using a wavelet transformation to separate each of the pre-processed sinograms 221 into high- and low-frequency components. Additionally, in still other implementations, the frequency splitting can be performed using any other transformation or frequency component separation method to separate the high- and low-frequency components, without departing from the spirit of disclosure.

In step 229, the high-frequency components of the high- and low-kV sinograms 221 are applied to a high-frequency neural network, and the low-frequency components of the high- and low-kV sinograms 221 are applied in parallel to a low-frequency neural network. Then, the high- and low-frequency sinograms resulting from the respective neural networks are combined (e.g., by summing) to generate the filtered high- and low-kV sinograms 227.

Figure 10:
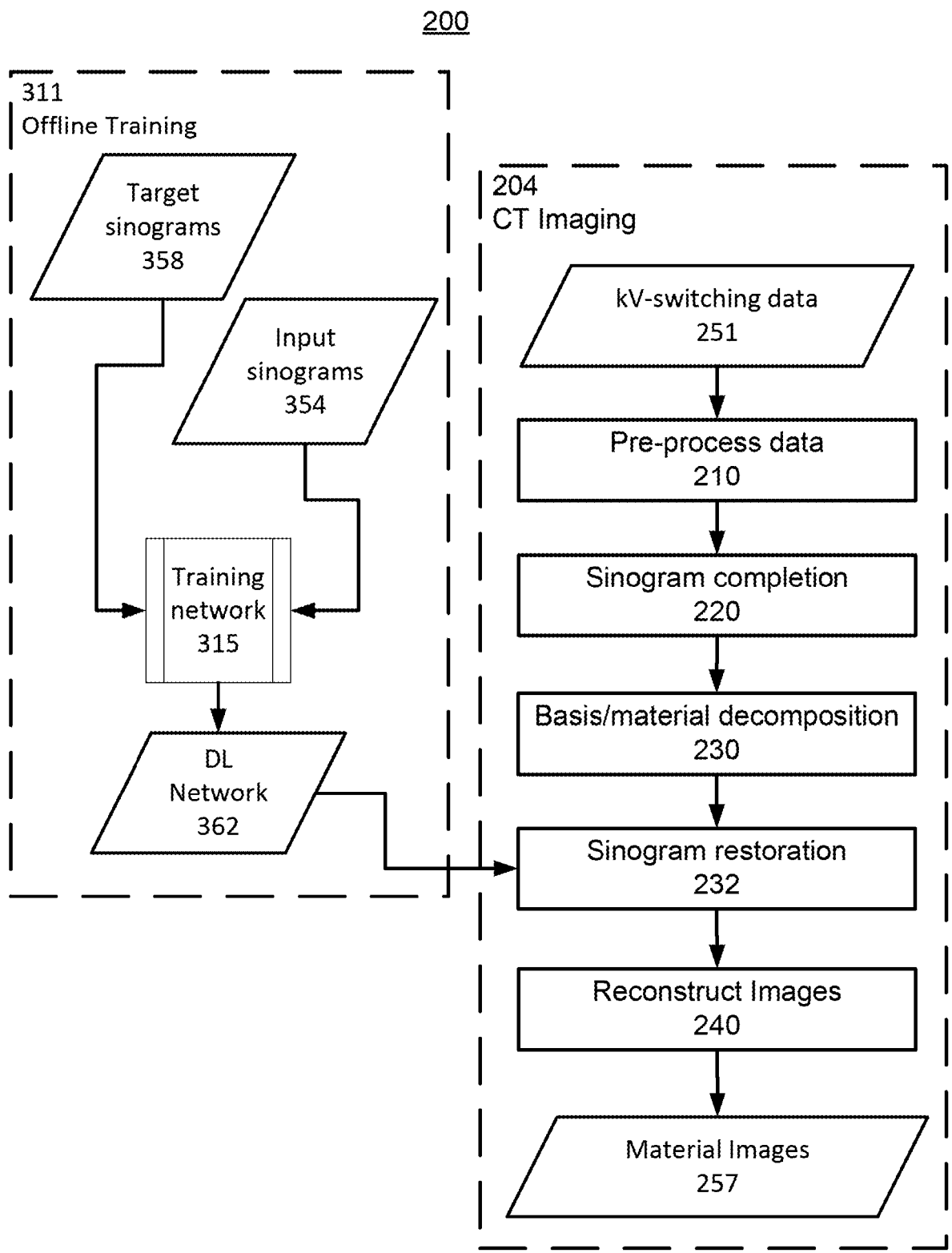
FIG. 10 shows an example of a flow diagram for training and using a DL ANN to perform sinogram restoration, according to one implementation.

FIG. 10 shows a flow diagram for a modified method 200 in which a DL-ANN network 362 is used in step 232 of process 204, which is performed after the basis decomposition in step 230 and before the reconstruction in step 240. Due to the nonlinear nature of the basis decomposition process, the residual error after sinogram completion may be amplified during decomposition and lead to appreciable errors in the reconstructed basis images. To cure these errors, the methods described herein can perform, in the basis decomposed domain (e.g., material component domain), deep learning based sinogram restoration, thereby minimizing the error in the basis-decomposed sinograms before image reconstruction. For example, this sinogram restoration can be performed at step 232 by applying the basis-component sinograms resulting from step 230 to the DL-ANN network 362 trained using process 311.

In step 220, sinogram completion is performed on the low- and high-kV sinograms to create full dual kV sinograms before basis decomposition. Step 220 can be performed using the DL-ANN network 361, as described with reference to FIG. 9A, or the sinogram completion can be performed using a interpolation approach, an inpainting approach, or any other method.

In step 230, the material/basis decomposition is performed as discussed above. The input sinograms 354 used to train the DL-ANN network 362 can be prepared using the same or similar process as the low- and high-kV sinograms resulting from step 230. The target sinograms are also prepared in a similar manner, except the target sinograms are prepared without sinogram completion because the target data are prepared from complete sinograms rather than from k-switching sinograms.

In step 232, the basis-component sinograms resulting from step 230 are applied to the trained DL-ANN network 362.

Figure 11:
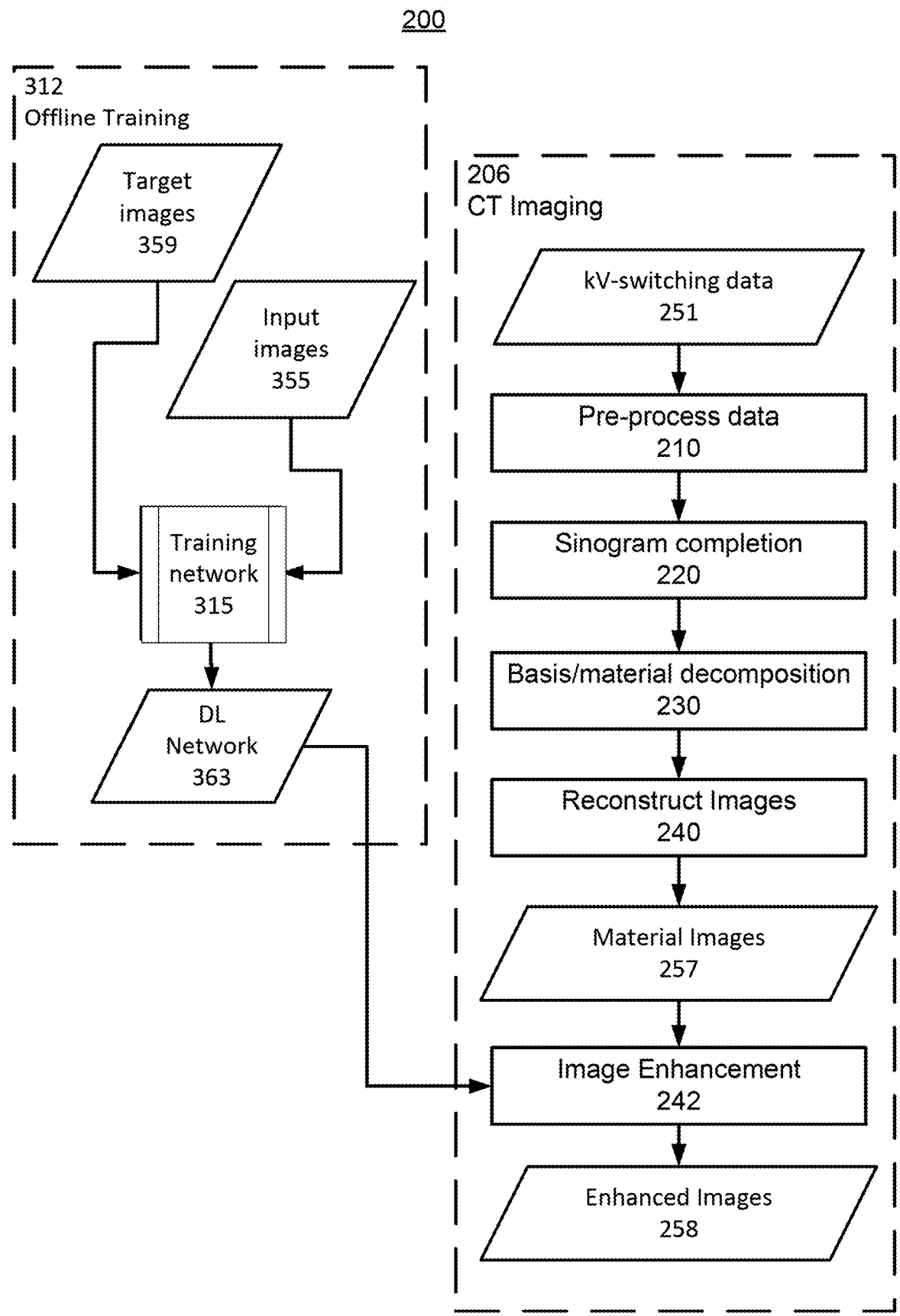
FIG. 11 shows an example of a flow diagram for training and using a DL ANN to perform image enhancement, according to one implementation.

FIG. 11 shows a flow diagram for a modified method 200 in which a DL-ANN network 363 is used in step 242 of process 206, after the reconstruction in step 240. To further improve the quality of reconstructed basis images, the methods described herein can use a deep learning based post-processing method in the image domain. The image reconstruction process of steps 210-240 is performed as described above (e.g., optionally using the DL-ANN network 361 at step 220 and optionally using the DL-ANN network 362 at step 232).

The input images 355 are prepared from kV-switching data using the same processing steps, and the target images 359 are prepared from complete sinogram data using the same processing steps, except those that are unique for sinogram completion and/or correcting errors deriving from incomplete sinogram data. In process 312, the DL-ANN network 363 is trained using the input images 355 and the target images 359.

In step 242, the basis-component images 257 from step 240 are applied to the trained DL-ANN network 363 to generate the enhanced basis-component images 258.

Figure 12:
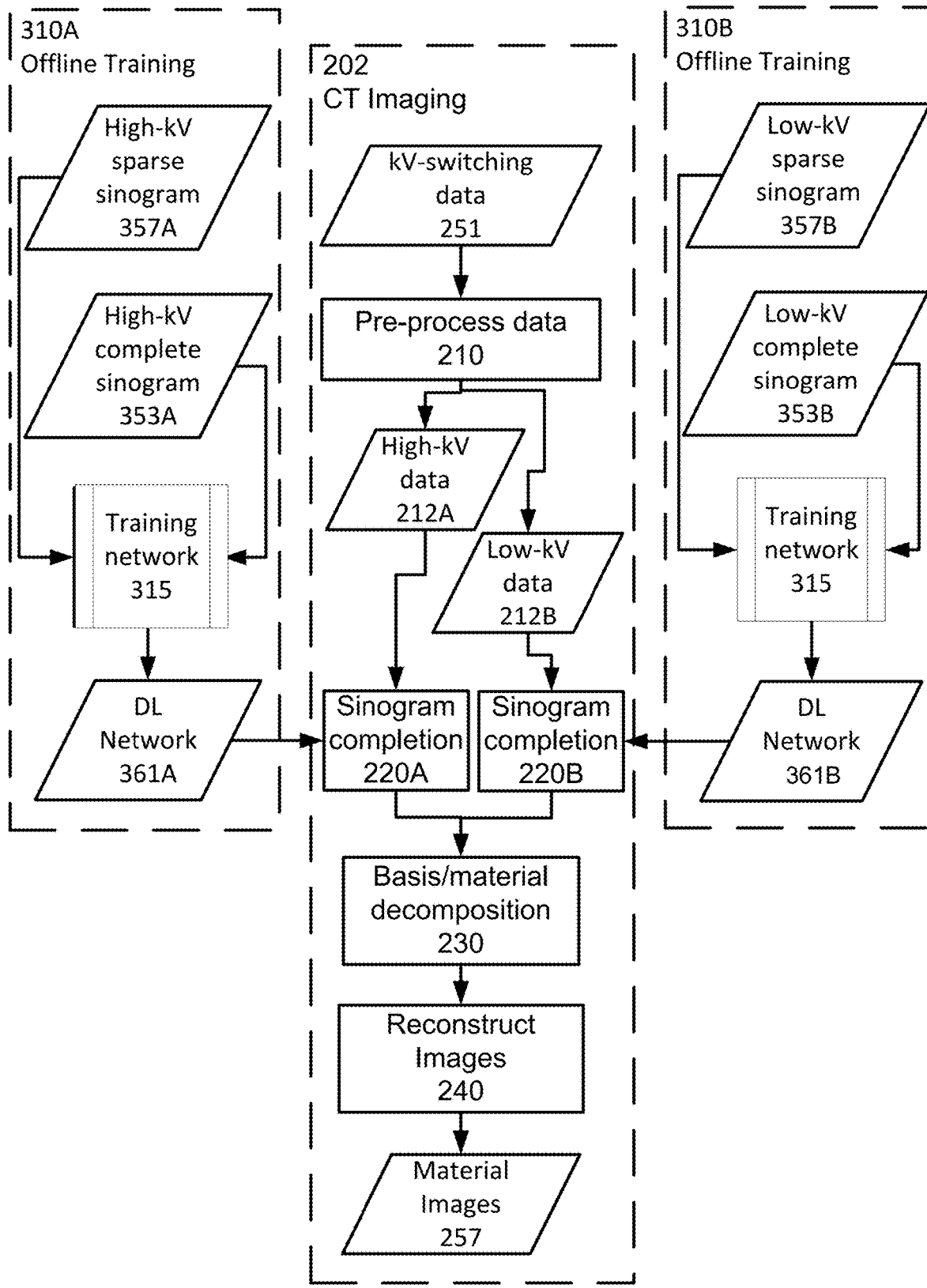
FIG. 12 shows an example of a flow diagram for training and using two a DL ANN to perform single channel sinogram completion respectively on the high-kV and low-kV sinograms, according to one implementation.

FIG. 12 shows a flow diagram for a modified method 200 in which two separate DL-ANN networks 361A and 361B are used in steps 220A and 220B respectively to perform/correct for sinogram completion. The flow diagram in FIG. 12 is the same as in FIG. 9A, except the high-kV sinogram and the low-kV sinogram are processed separately using separate DL-ANN networks 361A and 361B, rather than being processed together using a two-channel network in which the low- and high-kV sinograms are applied to the respective channels. That is, in process 310A, the DL-ANN networks 361A is trained using high-kV kV-switching sinograms to generate the input data and using high-kV complete sinograms as the target data. Further, in process 310B, the DL-ANN networks 361B is trained using low-kV kV-switching sinograms to generate the input data and using low-kV complete sinograms as the target data.

Because the DL-ANN networks 361A and 361B use only one or the other of the two kV-switching sinograms, each of the DL-ANN networks 361A and 361B do not have access to the complementary information provided by the other of the k-switching sinograms. Nevertheless, the DL-ANN network 361A (361B) can be used a two channel network by applying a mask that is the same dimensions as the sinograms as the second channel. The pre-processed high-kV (low-kV) sinogram is applied as the first channel. For example, the mask can use a value of "1" to indicate that a given pixel was absent in the original high-kV sinogram, and use a value of "0" to indicate that a given pixel was present in the original high-kV sinogram. This additional information can help the DL-ANN network 361A (361B) to achieve better performance. The mask can also be applied in one or more of the other DL-ANN networks 361, 362, and 363 as a third channel to provide additional information and thereby improve performance.

Additionally or alternatively, the mask can be applied to generate weights in a loss function that is used during offline training of the neural network(s). For example, pixel values that were initially absent from a kV-switching sinogram and are subsequently filled in during the sinogram completion process can be weighted more than values of the sinogram that were always present and have not been changed by the sinogram completion process. This weighting can improve convergence by favoring changes to the DL ANN networks that optimizes performance in the filled in regions of the sinograms.

In addition to the binary mask of "1" and "0" values discussed above, a distance mask can also be used. The distance mask would represent the distance between a missing measurement value and the closest non-missing measurement value. A greater mask value indicates the missing measurement is further away from the nearest measured value. For measured pixels of the kV-switching sinogram, a pixel in the mask can be assigned a "0" value. The distance mask can be used in a similar manner to how the binary mask is used, as described above.

In summary, dual-energy CT (DECT) has been developed and is increasingly accepted as an advanced imaging tool by radiologists. As compared to conventional single-energy CT scanners, DECT scanners have the capability of differentiating distinct materials even though they present similar HU values under single-energy CT. Implementation of DECT can be categorized into three major types: dual tube kV switching, dual x-ray source, and dual layer detector. For the kV switching acquisition method, at most one steady kV is available at each view. Given that measurements from two kVs are required to perform material decomposition in the sinogram space, sinogram completion is performed prior to material/basis decomposition.

Related approaches to address the issue of incomplete measurements, such as model-based iterative image reconstruction, are either time consuming or are only suitable for limited applications (e.g., when expensive hardware is used, such as in fast kV switching). Deep learning (DL) holds promise for applications such as image inpainting and completion tasks and might achieve better results than related inpainting methods. As compared to related methods, DL does not require explicit modelling, and instead relies on training data to learn an optimal approach to correct defects in the input data. DL can therefore be capable of capturing the inherent correlation between pixels, locally and globally, and build up a sophisticated network by training the network using a training dataset that includes inputs (e.g., corrupted observations) paired with targets (e.g., ground truth). To reduce computational time, hardware costs and further improve dual kV switching image quality, the methods described herein use a DL approach to complete the missing measurements in dual-energy CT with dual kV switching acquisition.

A DL ANN network can be used at various steps in the process of sinogram completion, material/basis decomposition, and image reconstruction. For example, a DL ANN network can be used during or immediately after sinogram completion to reduce errors and imperfections resulting from the sinogram completion. Further, a DL ANN network can be used during or after basis decomposition and/or image reconstruction to reduce/correct errors and artifacts due to residual imperfections resulting from the incomplete sinograms that are acquired during kV-switching. These DL ANN network can leverage the complementary information of the high- and low-kV sinograms to achieve better sinogram completion and improved image quality for the CT images reconstructed therefrom.

Several advantages can be achieved by the above-noted features. First, the DL ANN approaches are not only suitable for fast kV-switching implementations, but are also suitable for cases where slow (i.e., sparse) kV switching is adopted, that is, when more than one consecutive view is missing for a respective kV setting. That is, the above features enable sparse kV-switching implementations, which compared to fast kV-switching implementations, can be performed with less expensive hardware.

Second, the improvements realized by the DL ANN approaches described herein can improve the data sufficiently that reconstruction can be performed using a back-projection approach, as opposed to using an iterative reconstruction method to recover the missing data or reconstruct the images. Using a back-projection approach can drastically reduce the computational time and hardware cost.

Third, the DL ANN approaches described herein are intentionally tailored to DECT, rather than single-energy CT. Consequently, the methods described herein have three advantages not found in approaches directed toward single-energy CT. First, in certain implementations, the methods described herein employ a two-step, 2.5D sinogram processing strategy that reduces the computational time while maintaining the benefit of 3D processing. Second, the methods described herein can use frequency splitting to improve the efficiency and convergence of the offline training. Third, the methods described herein can be used with sinogram masks to improve performance.

Now a more detailed description of training a DL-ANN network is provided (e.g., process 315). This description is illustrated using the non-limiting example of the target data being the complete sinograms 353 and the input data being the sparse-view sinograms 357, but, in general, any target data and input data can be used.

Figure 13:
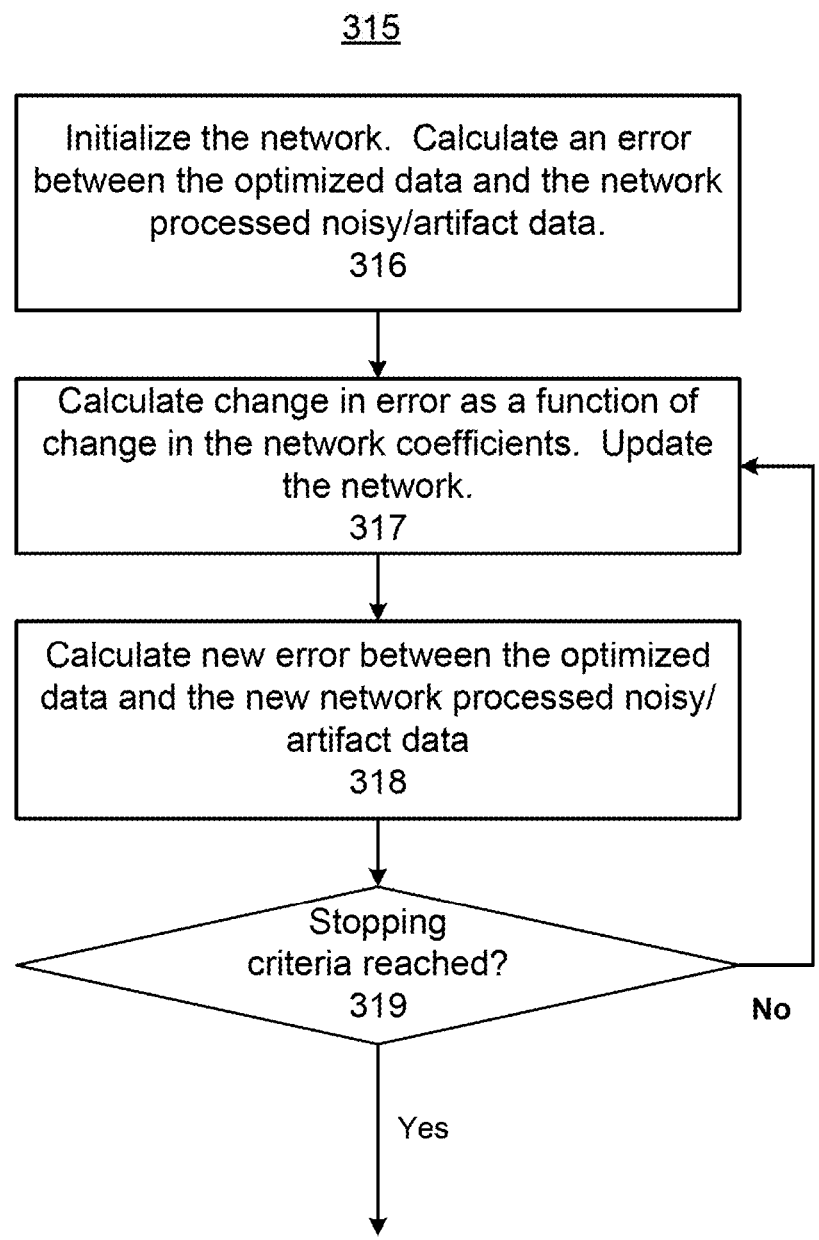
FIG. 13 shows a flow diagram of training a DL-ANN network by iteratively adjusting coefficients of the DL-ANN network to optimize a loss-error function, according to one implementation.

FIG. 13 shows a flow diagram of one implementation of the training process 315. In process 315, low-quality data 357 and high-quality data 353 are used as training data to train a DL-ANN network, resulting in the DL-ANN network being output from step 319 of process 315. In general, the data 357 can be any defect-exhibiting sinograms or images, for which the "defect" can be any undesirable characteristic that can be affected through image processing (e.g., noise or an artifact). Similarly, data 353 can be referred to as target data, defect-reduced data, defect-minimized data, or optimized data, for which the "defect" is less than in the images 357. The offline DL training process 315 trains the DL-ANN network 361 using a large number of input sinograms 357 that are paired with corresponding target sinograms 353 to train the DL-ANN network 361 to produce images resembling the target sinograms 353 from the input sinograms 357.

In process 315, a set of training data is obtained, and the network 361 is iteratively updated to reduce the error (e.g., the value produced by a loss function). The DL-ANN network infers the mapping implied by the training data, and the cost function produces an error value related to the mismatch between the target sinograms 353 and the result produced by applying a current incarnation of the DL-ANN network 361 to the input sinograms 357. For example, in certain implementations, the cost function can use the mean-squared error to minimize the average squared error. In the case of a multilayer perceptrons (MLP) neural network, the backpropagation algorithm can be used for training the network by minimizing the mean-squared-error-based cost function using a (stochastic) gradient descent method.

In step 316 of process 315, an initial guess is generated for the coefficients of the DL-ANN network 361. For example, the initial guess can be based on a priori knowledge of the region being imaged or one or more exemplary denoising methods, edge-detection methods, and/or blob detection methods. Additionally, the initial guess can be based on one of a LeCun initialization, an Xavier initialization, and a Kaiming initialization.

Steps 316 through 319 of process 315 provide a non-limiting example of an optimization method for training the DL-ANN network 361.

An error is calculated (e.g., using a loss function or a cost function) to represent a measure of the difference (e.g., a distance measure) between the target sinograms 353 (i.e., ground truth) and input sinograms 357 after applying a current version of the network 361. The error can be calculated using any known cost function or distance measure between the image data, including those cost functions described above. Further, in certain implementations the error/loss function can be calculated using one or more of a hinge loss and a cross-entropy loss.

Additionally, the loss function can be combined with a regularization approach to avoid overfitting the network to the particular instances represented in the training data. Regularization can help to prevent overfitting in machine learning problems. If trained too long, and assuming the model has enough representational power, the network will learn the noise specific to that dataset, which is referred to as overfitting. In case of overfitting, the DL-ANN becomes a poor generalization, and the variance will be large because the noise varies between datasets. The minimum total error occurs when the sum of bias and variance are minimal. Accordingly, it is desirable to reach a local minimum that explains the data in the simplest possible way to maximize the likelihood that the trained network represents a general solution, rather than a solution particular to the noise in the training data. This goal can be achieved, e.g., by early stopping, weight regularization, lasso regularization, ridge regularization, or elastic net regularization.

In certain implementations, the network 361 is trained using backpropagation. Backpropagation can be used for training neural networks and is used in conjunction with gradient descent optimization methods. During a forward pass, the algorithm computes the network's predictions based on the current parameters e. These predictions are then input into the loss function, by which they are compared to the corresponding ground truth labels (i.e., the high-quality image 353). During the backward pass, the model computes the gradient of the loss function with respect to the current parameters, after which the parameters are updated by taking a step size of a predefined size in the direction of minimized loss (e.g., in accelerated methods, such that the Nesterov momentum method and various adaptive methods, the step size can be selected to more quickly converge to optimize the loss function).

The optimization method by which the backprojection is performed can use one or more of gradient descent, batch gradient descent, stochastic gradient descent, and mini-batch stochastic gradient descent. Additionally, the optimization method can be accelerated using one or more momentum update techniques in the optimization approach that results in faster convergence rates of stochastic gradient descent in deep networks, including, e.g., Nesterov momentum technique or an adaptive method, such as Adagrad sub-gradient method, an Adadelta or RMSProp parameter update variation of the Adagrad method, and an Adam adaptive optimization technique. The optimization method can also apply a second order method by incorporating the Jacobian matrix into the update step.

The forward and backwards passes can be performed incrementally through the respective layers of the network. In the forward pass, the execution starts by feeding the inputs through the first layer, thus creating the output activations for the subsequent layer. This process is repeated until the loss function at the last layer is reached. During the backward pass, the last layer computes the gradients with respect to its own learnable parameters (if any) and also with respect to its own input, which serves as the upstream derivatives for the previous layer. This process is repeated until the input layer is reached.

Returning to FIG. 13, step 317 of process 315 determines a change in the error as a function of the change in the network can be calculated (e.g., an error gradient), and this change in the error can be used to select a direction and step size for a subsequent change to the weights/coefficients of the DL-ANN network 361. Calculating the gradient of the error in this manner is consistent with certain implementations of a gradient descent optimization method. In certain other implementations, this step can be omitted and/or substituted with another step in accordance with another optimization algorithm (e.g., a non-gradient descent optimization algorithm like simulated annealing or a genetic algorithm), as would be understood by one of ordinary skill in the art.

In step 317 of process 315, a new set of coefficients are determined for the DL-ANN network 361. For example, the weights/coefficients can be updated using the change calculated in step 317, as in a gradient descent optimization method or an over-relaxation acceleration method.

In step 318 of process 315, a new error value is calculated using the updated weights/coefficients of the DL-ANN network 361.

In step 319, predefined stopping criteria are used to determine whether the training of the network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations is reached. When the stopping criteria are not satisfied the training process performed in process 315 will continue back to the start of the iterative loop by returning and repeating step 317 using the new weights and coefficients (the iterative loop includes steps 317, 318, and 319). When the stopping criteria are satisfied the training process performed in process 315 is completed.

Figure 14A:
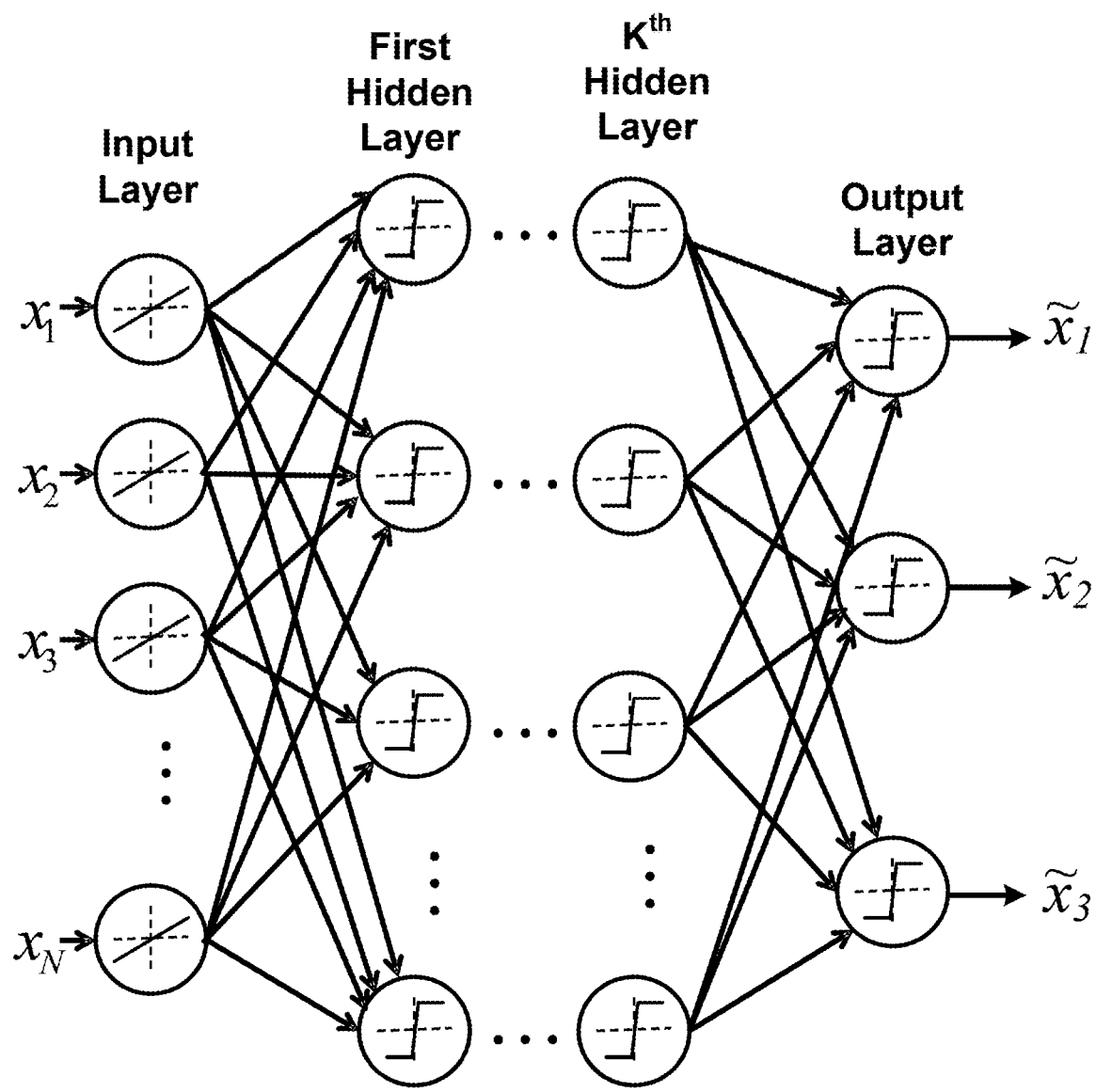
FIG. 14A shows an example of a feedforward ANN, according to one implementation.
Figure 14B:
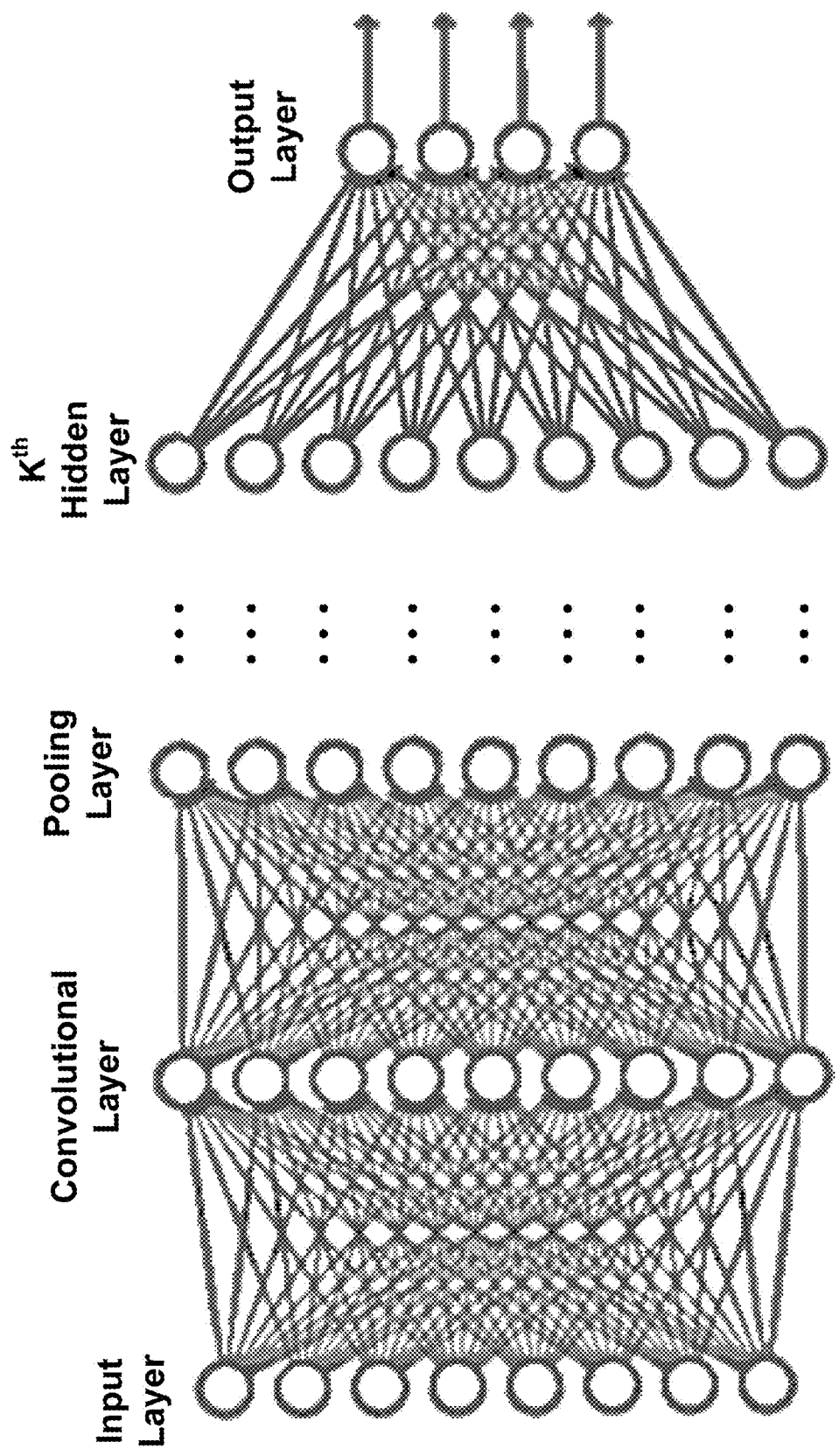
FIG. 14B shows an example of a type of ANN referred to as a convolutional neural network (CNN), according to one implementation.

FIGS. 14A and 14B show various examples of the interconnections between layers in the DL-ANN network 361. The DL-ANN network 361 can include fully connected, convolutional, and the pooling layer, all of which are explained below. In certain preferred implementations of the DL-ANN network 361, convolutional layers are placed close to the input layer, whereas fully connected layers, which perform the high-level reasoning, are placed further down the architecture towards the loss function. Pooling layers can be inserted after convolutions and provide a reduction lowering the spatial extent of the filters, and thus the amount of learnable parameters. Activation functions are also incorporated into various layers to introduce nonlinearity and enable the network to learn complex predictive relationships. The activation function can be a saturating activation functions (e.g., a sigmoid or hyperbolic tangent activation function) or rectified activation function (e.g., the Rectified Linear Unit (ReLU) applied in the first and second examples discussed above). The layers of the DL-ANN network 361 can also incorporate batch normalization, as also exemplified in the first and second examples discussed above.

FIG. 14A shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The simplest ANN has three layers, and is called an autoencoder. The DL-ANN network 361 can have more than three layers of neurons, and has as many outputs neurons $\tilde{x}_N$ as input neurons, wherein N is the number of pixels in the reconstructed image. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m(x) is defined as a composition of other functions $n_i(x)$, which can further be defined as a composition of other functions. This can be conveniently represented as a network structure, with arrows depicting the dependencies between variables, as shown in FIG. 14A. For example, the ANN can use a nonlinear weighted sum, wherein $m(x)=K(\Sigma_i w_i n_i(x))$, where K (commonly referred to as the activation function) is some predefined function, such as the hyperbolic tangent.

In FIG. 14A (and similarly in FIG. 14B), the neurons (i.e., nodes) are depicted by circles around a threshold function. For the non-limiting example shown in FIG. 14A, the inputs are depicted as circles around a linear function, and the arrows indicate directed connections between neurons. In certain implementations, the DL-ANN network 361 is a feedforward network.

FIG. 14B shows a non-limiting example in which the DL-ANN network 361 is a convolutional neural network (CNN). CNNs are type of ANN that has beneficial properties for image processing, and, therefore, have specially relevancy for the applications of image denoising. CNNs use feed-forward ANNs in which the connectivity pattern between neurons can represent convolutions in image processing. For example, CNNs can be used for image-processing optimization by using multiple layers of small neuron collections which process portions of the input image, called receptive fields. The outputs of these collections can then be tiled so that they overlap, to obtain a better representation of the original image. This processing pattern can be repeated over multiple layers having alternating convolution and pooling layers.

Following after a convolutional layer, a CNN can include local and/or global pooling layers, which combine the outputs of neuron clusters in the convolution layers. Additionally, in certain implementations, the CNN can also include various combinations of convolutional and fully connected layers, with pointwise nonlinearity applied at the end of or after each layer.

CNNs have several advantages for image processing. To reduce the number of free parameters and improve generalization, a convolution operation on small regions of input is introduced. One significant advantage of certain implementations of CNNs is the use of shared weight in convolutional layers, which means that the same filter (weights bank) is used as the coefficients for each pixel in the layer; this both reduces memory footprint and improves performance. Compared to other image-processing methods, CNNs advantageously use relatively little pre-processing. This means that the network is responsible for learning the filters that in traditional algorithms were hand-engineered. The lack of dependence on prior knowledge and human effort in designing features is a major advantage for CNNs.

Figure 15:
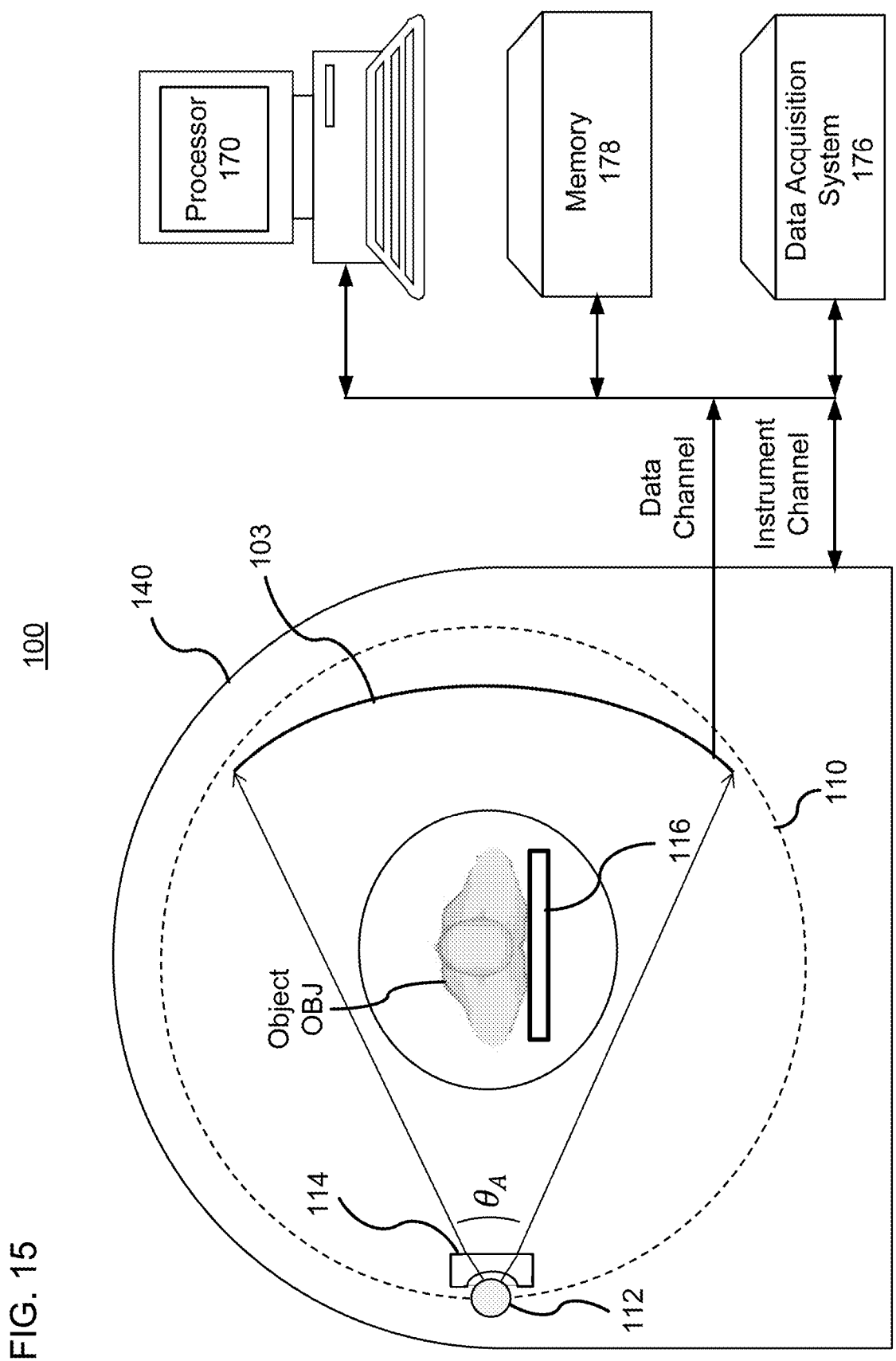
FIG. 15 shows a first example of computed tomography (CT) scanner for sparse kV-switching, according to one implementation.

FIG. 15 shows a first implementation of a computed tomography (CT) scanner having energy-integrating detectors arranged in a third-generation geometry. The diagram illustrates relative positions among the X-ray source 112, the collimator/filter 114, the X-ray detector 103, and the photon-counting detectors PCD1 through PCDN.

In addition to the configuration of the X-ray source 112 and the detector unit 103 shown in FIG. 15, other types and combinations of X-ray detectors and X-ray source can be used to obtain the projection data.

FIG. 15 also shows circuitry and hardware for acquiring, storing, processing, and distributing X-ray projection data. The circuitry and hardware include: a processor 170, a memory 178, and a data acquisition system 176.

As the X-ray source 112 and the detector unit 103 are housed in a gantry 140 and rotate around circular path of the rotational component 110. The detector elements in the detector unit 103 detect the X-ray radiation that has been transmitted and output the detected signals as the detector unit 103 rotates. In one implementation, the detector unit 103 has densely placed energy-integrating detectors in predetermined channel and segment directions on the detector unit surface.

In one implementation, the X-ray source 112 is optionally a single X-ray source that is configured to perform a k-switching function for emitting X-ray radiation at a predetermined high-level energy and at a predetermined low-level energy.

The detector unit 103 can use energy integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline, an organic liquid, a plastic, or other known scintillator.

The CT scanner also includes a data channel that routes projection measurement results from the photon-counting detectors and the detector unit 103 to a data acquisition system 176, a processor 170, and memory 178. The data acquisition system 176 controls the acquisition, digitization, and routing of projection data from the detectors. The data acquisition system 176 also includes radiography control circuitry to control the rotation of the annular rotating frame 110. In one implementation data acquisition system 176 will also control the movement of the bed 116, the operation of the X-ray source 112, and the operation of the X-ray detectors 103. The data acquisition system 176 can be a centralized system or alternatively it can be a distributed system. In an implementation, the data acquisition system 176 is integrated with the processor 170. The processor 170 performs functions including reconstructing images from the projection data, pre-reconstruction processing of the projection data, and post-reconstruction processing of the image data. The processor 170 also performs the functions and methods described herein.

The pre-reconstruction processing of the projection data can include correcting for detector calibrations, detector nonlinearities, polar effects, noise balancing, and material decomposition. Additionally, the pre-reconstruction processing can include various processing in step 210.

Post-reconstruction processing can include filtering and smoothing the image, volume rendering processing, and image difference processing as needed. Additionally, the post-reconstruction processing can be performed after step 240 in the various implementations of method 200, including process 202, 204, 206, 310, 310A, 310B, 311 and 312.

The image-reconstruction process can be performed using filtered back-projection, iterative-image-reconstruction methods, or stochastic-image-reconstruction methods. Additionally, the image-reconstruction processing can include step 220.

Both the processor 170 and the data acquisition system 176 can make use of the memory 178 to store, e.g., projection data, reconstructed images, calibration data and parameters, and computer programs.

The processor 170 can include a CPU and a network controller. The CPU can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art. The network controller can be, e.g., an Intel Ethernet PRO network interface card from Intel Corporation of America, can interface between the various parts of the CT scanner. Additionally, the network controller can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

The memory 178 can be a hard disk drive, CD-ROM drive, DVD drive, FLASH drive. RAM, ROM or any other electronic storage known in the art.

Figure 16:
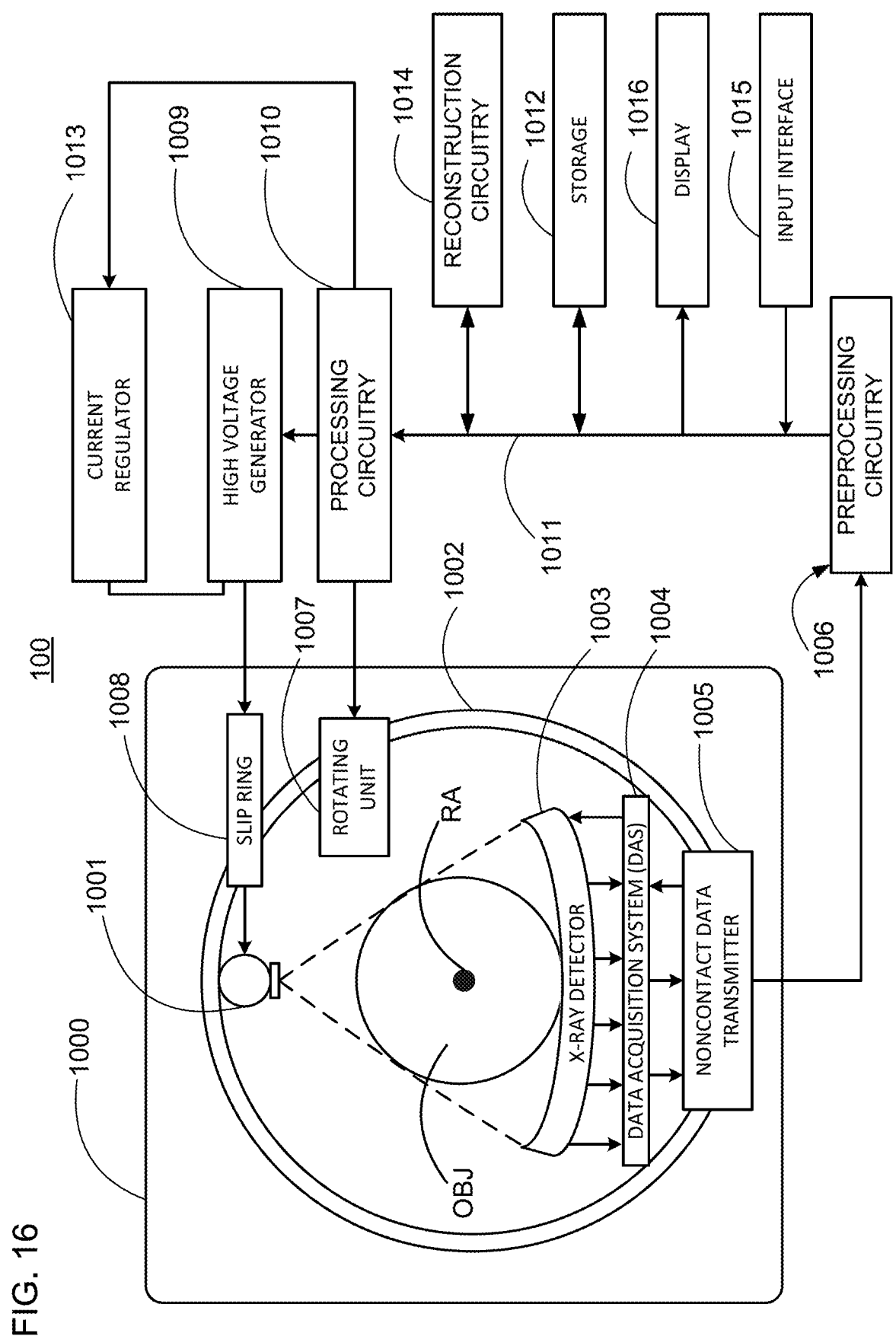
FIG. 16 shows a second example of CT scanner for sparse kV-switching, according to one implementation.

FIG. 16 illustrates a second implementation of the radiography gantry included in a CT apparatus or scanner 100. As shown in FIG. 16, a radiography gantry 1000 is illustrated from a side view and further includes an X-ray tube 1001, an annular frame 1002, and a multi-row or two-dimensional-array-type X-ray detector 1003. The X-ray tube 1001 and X-ray detector 1003 are diametrically mounted across an object OBJ on the annular frame 1002, which is rotatably supported around a rotation axis RA. A rotating unit 1007 rotates the annular frame 1002 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, will be exemplified.

The multi-slice X-ray CT apparatus further includes a high voltage generator 100) that generates a tube voltage applied to the X-ray tube 1001 through a slip ring 1008 so that the X-ray tube 1001 generates X-rays. The X-rays are emitted towards the object OBJ, whose cross sectional area is represented by a circle. For example, the X-ray tube 1001 having an average X-ray energy during a first scan that is less than an average X-ray energy during a second scan. Thus, two or more scans can be obtained corresponding to different X-ray energies. The X-ray detector 1003 is located at an opposite side from the X-ray tube 1001 across the object OBJ for detecting the emitted X-rays that have transmitted through the object OBJ. The X-ray detector 1003 further includes individual detector elements or units.

The CT apparatus further includes other devices for processing the detected signals from X-ray detector 1003. A data acquisition circuit or a Data Acquisition System (DAS) 1004 converts a signal output from the X-ray detector 1003 for each channel into a voltage signal, amplifies the signal, and further converts the signal into a digital signal. The X-ray detector 1003 and the DAS 1004 are configured to handle a predetermined total number of projections per rotation (TPPR).

The above-described data is sent to a preprocessing circuitry 1006, which is housed in a console outside the radiography gantry 1000 through a non-contact data transmitter 1005. The preprocessing circuitry 1006 performs certain corrections, such as sensitivity correction on the raw data. A storage 1012 stores the resultant data, which is also called projection data at a stage immediately before reconstruction processing. The storage 1012 is connected to a processing circuitry 1010 through a data/control bus 1011, together with a reconstruction device 1014, input interface 1015, and display 1016. The processing circuitry 1010 controls a current regulator 1013 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 1001 and the X-ray detector 1003 are diametrically mounted on the annular frame 1002 and are rotated around the object OBJ as the annular frame 1002 is rotated about the rotation axis RA. In the fourth-generation geometry system, the detectors are fixedly placed around the patient and an X-ray tube rotates around the patient. In an alternative embodiment, the radiography gantry 1000 has multiple detectors arranged on the annular frame 1002, which is supported by a C-arm and a stand.

The storage 1012 can store the measurement value representative of the irradiance of the X-rays at the X-ray detector unit 1003. Further, the storage 1012 can store a dedicated program for executing the methods described herein (e.g., method 200 and variations thereof).

The reconstruction circuitry 1014 can execute various steps of methods described herein (e.g., step 220 of method 200 and variations thereof). Further, reconstruction circuitry 1014 can execute pre-reconstruction processing image processing such as volume rendering processing and image difference processing as needed.

The pre-reconstruction processing of the projection data performed by the preprocessing circuitry 1006 can include correcting for detector calibrations, detector nonlinearities, and polar effects, for example. Further, the pre-reconstruction processing can include step 210.

Post-reconstruction processing performed by the reconstruction circuitry 1014 can include filtering and smoothing the image, volume rendering processing, and image difference processing as needed. The image reconstruction process can implement various steps of method 200 (e.g., steps 230 and 240) and also the offline training of the DL-ANN networks (e.g., process 310, 320, and 330). The reconstruction circuitry 1014 can use the memory to store, e.g., projection data, reconstructed images, calibration data and parameters, and computer programs.

The reconstruction circuitry 1014 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the storage 1012 can be non-volatile, such as ROM, EPROM, EEPROM or FLASH memory. The storage 1012 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction circuitry 1014 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 1016. The display 1016 can be an LCD display, CRT display, plasma display, OLED, LED or any other display known in the art.

The storage 1012 can be a hard disk drive, CD-ROM drive, DVD drive. FLASH drive, RAM, ROM or any other electronic storage known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. A data processing apparatus for multi-energy CT imaging, comprising:
processing circuitry configured to
obtain a set of projection data including interleaved low-kV and high-kV sparse projection data acquired in an X-ray CT scan of an object to be imaged, wherein during the CT scan, a voltage applied to an X-ray source used in the CT scan alternates between a first voltage and a second voltage higher than the first voltage, the first voltage corresponding to the low-kV sparse projection data, the second voltage corresponding to the high-kV sparse projection data; and
obtain a generated complete set of low-kV projection data and a generated complete set of high-kV projection data based on the obtained set of projection data, using one or more neural networks trained for completion of missing projection data, the one or more neural networks trained with multiple complete sets of low-kV projection data and multiple complete sets of high-kV projection data which are acquired in CT scans.

2. The data processing apparatus of claim 1, wherein one of the one or more neural networks receives both the low-kV sparse projection data and the high-kV sparse projection data.

3. The data processing apparatus of claim 2, wherein the low-kV sparse projection data is acquired during a period in which the first voltage is applied to the X-ray source, and the high-kV sparse projection data is acquired during a period in which the second voltage is applied to the X-ray source.

4. The data processing apparatus of claim 1, wherein the set of projection data includes projection data acquired during transition between a period in which the first voltage is applied to the X-ray source and a period in which the second voltage is applied to the X-ray source.

5. The data processing apparatus of claim 1, wherein the processing circuitry is configured to obtain the generated complete sets of low-kV and the high-kV projection data, based on the one or more neural networks for low-frequency components.

6. The data processing apparatus of claim 1, wherein the processing circuitry is configured to, in obtaining the generated complete sets of low-kV and high-kV projection data:
perform sinogram completion to the set of projection data to obtain processed low-kV projection data and processed high-kV projection data;
obtain a first low frequency component of the processed low-kV projection data and a second low frequency component of the processed high-kV projection data;

apply a first neural network to the first low frequency component to obtain a first processed low frequency component, and apply a second neural network to the second low frequency component to obtain a second processed low frequency component; and obtain the generated complete set of low-kV projection data and the generated complete set of high-kV projection data, based on the first processed low frequency component and the second processed low frequency component.

7. The data processing apparatus of claim 1, wherein the processing circuitry is further configured to perform material decomposition processing using the generated complete sets of low-kV and high-kV projection data to obtain multiple sets of basis component sinograms.

8. The data processing apparatus of claim 7, wherein the processing circuitry is further configured to perform reconstruction using the multiple sets of basis component sinograms to obtain multiple images.

9. The data processing apparatus of claim 8, wherein the processing circuitry is further configured to apply another one or more neural networks to the multiple images to obtain processed images.

10. The data processing apparatus of claim 9, wherein the another one or more neural networks are trained with multiple target images reconstructed from multiple complete sets of low-kV projection data and complete sets of high-kV projection data which are acquired in CT scans.

11. A data processing method for multi-energy CT imaging, comprising:

obtaining a set of projection data including interleaved low-kV and high-kV sparse projection data acquired in an X-ray CT scan of an object to be imaged, wherein during the CT scan, voltage applied to an X-ray source used in the CT scan alternates between a first voltage and a second voltage higher than the first voltage, the first voltage corresponding to the low-kV sparse projection data, the second voltage corresponding to the high-kV sparse projection data; and obtaining a generated complete set of low-kV projection data and a generated complete set of high-kV projection data based on the obtained set of projection data, using one or more neural networks trained for completion of missing projection data, the one or more neural networks trained with multiple complete sets of low-kV projection data and complete sets of high-kV projection data which are acquired in CT scans.

12. The data processing method of claim 11, wherein one of the one or more neural networks receives both the low-kV sparse projection data and the high-kV sparse projection data.

13. The data processing method of claim 12, wherein the low-kV sparse projection data is acquired during a period in which the first voltage is applied to the X-ray source, and the high-kV sparse projection data is acquired during a period in which the second voltage is applied to the X-ray source.

14. The data processing method of claim 11, wherein the set of projection data includes projection data acquired during transition between a period in which the first voltage is applied to the X-ray source and a period in which the second voltage is applied to the X-ray source.

15. The data processing method of claim 11, wherein the generated complete sets of low-kV and the high-kV projection data are obtained based on the one or more neural networks for low-frequency components.

16. The data processing method of claim 11, wherein obtaining the generated complete sets of low-kV and high-kV projection data comprises:

performing sinogram completion to the set of projection data to obtain processed low-kV projection data and processed high-kV projection data;

obtaining a first low frequency component of the processed low-kV projection data and a second low frequency component of the processed high-kV projection data;

applying a first neural network to the first low frequency component to obtain a first processed low frequency component, and apply a second neural network to the second low frequency component to obtain a second processed low frequency component; and obtaining the generated complete set of low-kV projection data and the generated complete set of high-kV projection data, based on the first processed low frequency component and the second processed low frequency component.

17. The data processing method of claim 11, further comprising:

performing material decomposition processing using the generated complete sets of low-kV and high-kV projection data to obtain multiple sets of basis component sinograms.

18. The data processing method of claim 17, further comprising:

performing reconstruction using the multiple sets of basis component sinograms to obtain multiple images.

19. The data processing method of claim 18, further comprising:

applying another one or more neural networks to the multiple images to obtain processed images.

20. The data processing method of claim 19, wherein the another one or more neural networks are trained with multiple target images reconstructed from multiple complete sets of low-kV projection data and complete sets of high-kV projection data which are acquired in CT scans.

\* \* \* \* \*